United States Patent [19]

Teraji et al.

[11] Patent Number: 4,585,872
[45] Date of Patent: Apr. 29, 1986

[54] CEPHEM INTERMEDIATES

[75] Inventors: Tsutomu Teraji, Osaka; Kazuo Sakane, Amagasaki; Jiro Gotto, Suita, all of Japan

[73] Assignee: Fujisawa Pharmaceutical Co., Ltd., Osaka, Japan

[21] Appl. No.: 571,380

[22] Filed: Jan. 16, 1984

Related U.S. Application Data

[62] Division of Ser. No. 213,351, Dec. 5, 1980, Pat. No. 4,447,429, which is a division of Ser. No. 50,216, Jun. 20, 1979, Pat. No. 4,268,509.

[30] Foreign Application Priority Data

Jul. 10, 1978 [GB] United Kingdom ............... 29357/78
Dec. 29, 1978 [GB] United Kingdom ............... 50334/78

[51] Int. Cl.$^4$ ........................................... C07D 285/08
[52] U.S. Cl. ..................................................... 548/128
[58] Field of Search ......................................... 548/128

[56] References Cited

U.S. PATENT DOCUMENTS 3,903,113  9/1975  Bradshaw et al. .................. 548/128
4,468,515  8/1984  Teraji .................................. 548/128

*Primary Examiner*—Robert Gerstl
*Attorney, Agent, or Firm*—Oblon, Fisher, Spivak, McClelland & Maier

[57] ABSTRACT

Alkoxyimino-2-(5-amino-1,2,4-thiadiazol-3-yl) acetic acid compounds are intermediates for cephem compounds.

9 Claims, No Drawings

CEPHEM INTERMEDIATES

This application is a division of application Ser. No. 213,351, filed Dec. 5, 1980, now U.S. Pat. No. 4,447,429, which in turn is a division of application Ser. No. 50,216, filed June 20, 1979, now U.S. Pat. No. 4,268,509.

This invention relates to new cephem compounds. More particularly, it relates to new 7-substituted-3-cephem-4-carboxylic acid and pharmaceutically acceptable salt thereof, which have antimicrobial activities, and processes for preparation thereof, to intermediate for preparing the same and processes for preparation thereof, and to pharmaceutical composition comprising the same and methods of using the same prophylactically and therapeutically for treatment of infectious diseases in human being and animals.

Accordingly, the objects of this invention are to provide:

new 7-substituted-3-cephem-4-carboxylic acid and pharmaceutically acceptable salt thereof, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals; and further intermediate to be used for preparation of pharmaceutically active 7-substituted-3-cephem-4-carboxylic acid or pharmaceutically acceptable salt thereof and processes for preparation thereof.

The object 7-substituted-3-cephem-4-carboxylic acid is novel and can be represented by the following general formula (I).

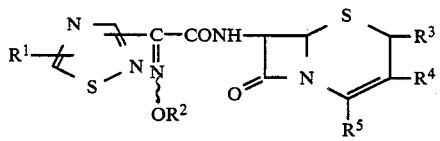

wherein
$R^1$ is amino or a protected amino,
$R^2$ is lower alkyl,
$R^3$ is hydrogen or lower alkyl,
$R^4$ is hydrogen, acyloxy(lower)alkyl, acylthio(lower)alkyl or a heterocyclicthio(lower)alkyl which may be substituted with suitable substituent(s) and
$R^5$ is carboxy or a protected carboxy.

According to the present invention, the object 7-substituted-3-cephem-4-carboxylic acid (I) can be prepared by the following processes.

Process 1

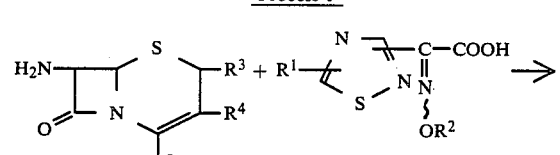

(II)
or its reactive derivative at the amino group or a salt thereof (III)
or its reactive derivative at the carboxy group or a salt thereof

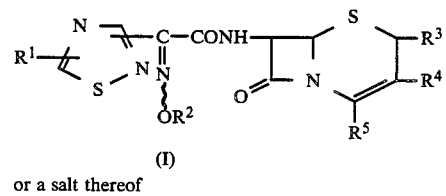

(I)
or a salt thereof

Process 2

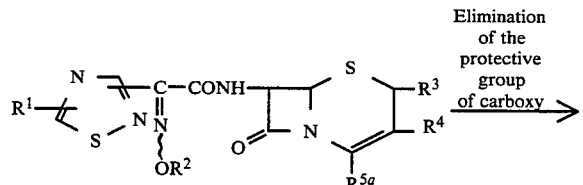

Elimination of the protective group of carboxy (Ia)
or a salt thereof

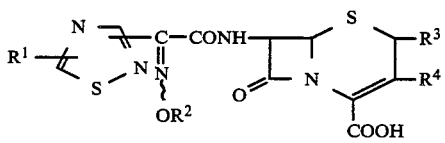

(Ib)
or a salt thereof

Process 3

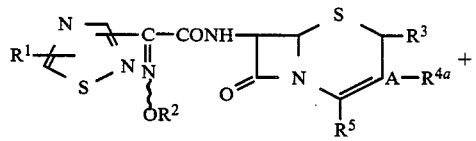

(Ic)
or a salt thereof

(IV)
or its reactive derivative at the mercapto group

3

-continued
Process 3

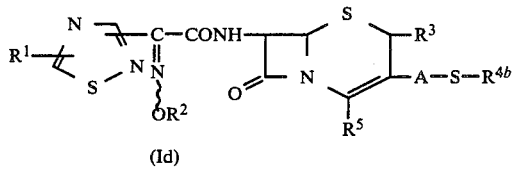

(Id)
or a salt thereof

Process 4

4

$R^1$, $R^2$, $R^3$, $R^4$ and $R^5$ are each as defined above;
$R^{5a}$ is a protected carboxy;
$R^{4a}$ is a group which can be substituted by a group $R^{4b}$—S— wherein $R^{4b}$ is acyl or a heterocyclic group which may be substituted with suitable substituent(s);
A is lower alkylene;
$R^{4b}$ is as defined above;
$R^{4c}$ is a heterocyclicthio(lower)alkyl substituted with protected amino(lower)alkyl or protected amino; and
$R^{4d}$ is a heterocyclicthio(lower)alkyl substituted with amino(lower)alkyl or amino.

Among the starting compounds of the present invention, the compound (III) is novel and can be prepared by the following preparations.

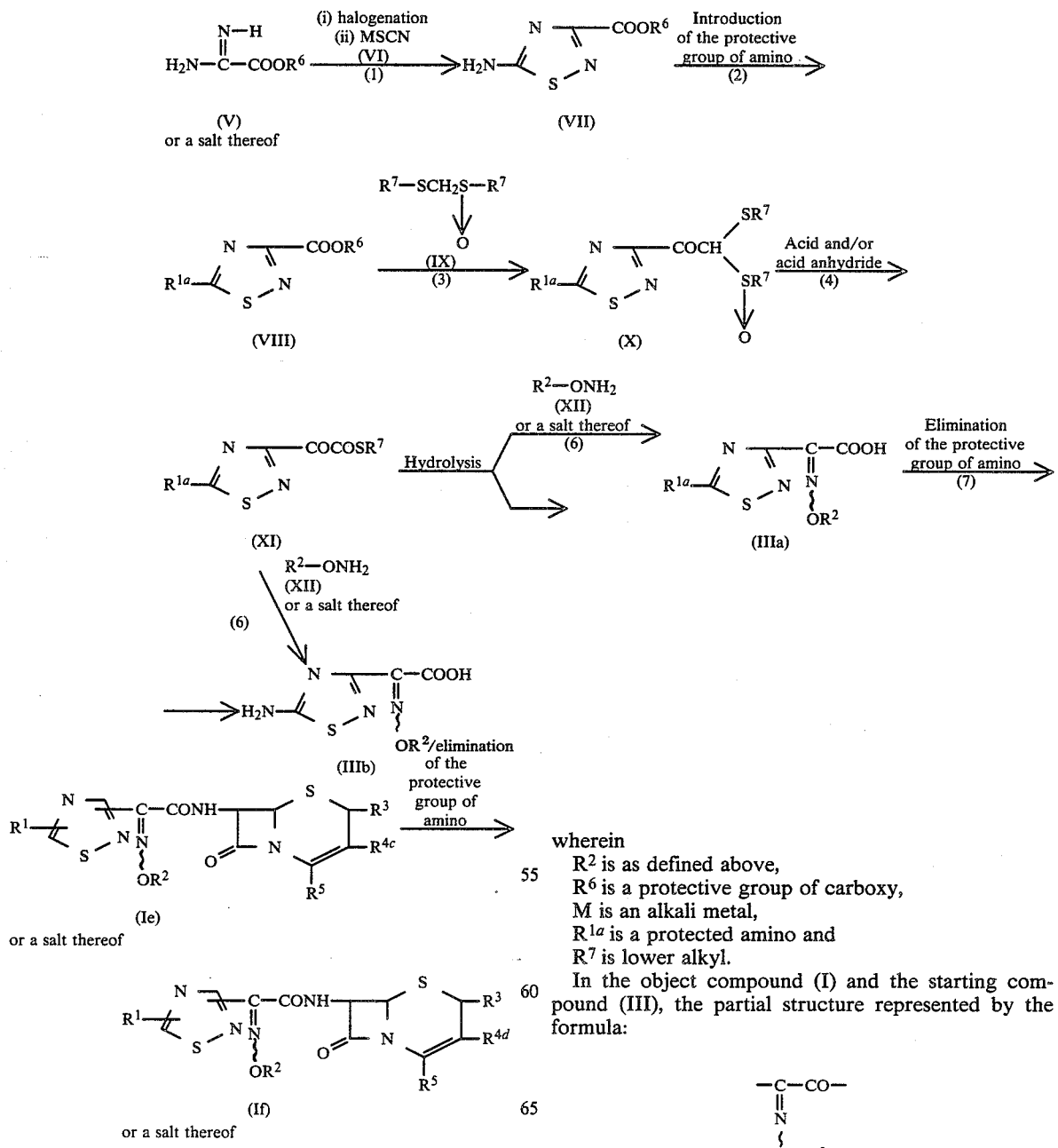

(Ie)
or a salt thereof

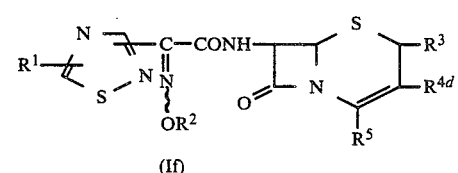

(If)
or a salt thereof wherein wherein
$R^2$ is as defined above,
$R^6$ is a protective group of carboxy,
M is an alkali metal,
$R^{1a}$ is a protected amino and
$R^7$ is lower alkyl.

In the object compound (I) and the starting compound (III), the partial structure represented by the formula:

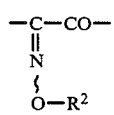

is to be understood to include both of the geometrical structures represented by the formulae:

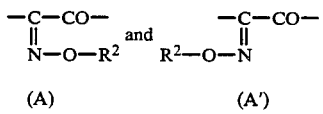

In this specification, with regard to all the compounds having the above mentioned partial structure, the compounds having the geometrical structure shown by the formula (A) are referred to as "syn isomer" and the compounds having the alternative one shown by the formula (A') as "anti isomer".

Regarding the object compound of the formula (I) and the starting compound of the formula (III) as mentioned above, it is also to be understood that said object and starting compounds may include tautomeric isomers relating to their thiadiazolyl group. That is, in case that the group represented by the formula:

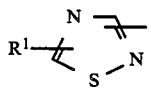

(wherein $R^1$ is amino or a protected amino) in formula of said object and starting compounds take the formula:

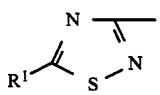

(wherein $R^1$ is as defined above), said group of the formula:

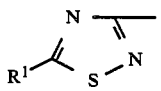

may be also alternatively represented by its tautomeric formula:

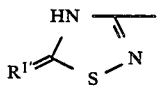

(wherein $R^{1'}$ is imino or a protected imino). That is, both of the said group (B) and (B') may be in the state of equilibrium as so-called tautomeric forms which can be represented by the following equilibrium:

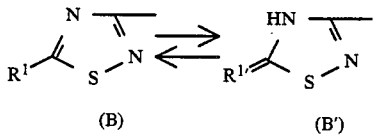

(wherein $R^1$ and $R^{1'}$ are each as defined above).

In the present specification including claims and examples, the object and starting compounds having said group are represented by using one of the expressions therefor, namely the formula:

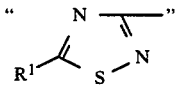

only for the convenient sake.

Suitable pharmaceutically acceptable salts of the object compound (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc.; an organic salt, for example, an organic amine salt (e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino)methane salt, phenylethylbenzylamine salt, dibenzylethylenediamine salt, etc.) etc.: an organic carboxylic or sulfonic acid salt (e.g., acetate, maleate, tartrate, methanesulfonate, benzenesulfonate, toluenesulfonate, etc.); an inorganic acid salt (e.g., hydrochloride, hydrobromide, sulfate, phosphate, etc.); a salt with a basic or acidic amino acid (e.g., arginine, aspartic acid, glutamic acid, lysine, etc.) and the like.

In the above and subsequent descriptions of the present specification, suitable examples and illustration of the various definitions which the present invention intends to include within the scope thereof are explained in detail as follows.

The term "lower" is used to intend a group having 1 to 6 carbon atom(s), unless otherwise provided.

Suitable protected amino may include an acylamino and amino group substituted by a conventional proptective group other than the acyl group, such as ar(lower)alkyl(e.g., benzyl, trityl, etc.) ar(lower)alkylidene(e.g., benzylidene, etc.), lower alkylidene substituted with lower alkoxycarbonyl or di(lower)alkylamino(e.g., 1-ethoxycarbonyl-2-propylidene, dimethylaminomethylene, etc.), phosphono or the like.

Suitable protected imino may include an acylimino and imino group substituted by a conventional protective group other than the acyl group such as aforesaid ar(lower)alkyl or the like.

Suitable acyl and acyl moiety in the terms "acylamino", "acylimino", "acyloxy(lower)alkyl" and "acylthio(lower)alkyl" may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s); lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms; lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.); ar(lower)alkanoyl (e.g., phenylacetyl, phenylpropionyl, etc.); ar(lower)alkoxycarbonyl (e.g. benzyloxycarbonyl, phenethyloxycarbonyl, etc.); and the like.

The acyl and acyl moiety as stated above may have 1 to 3 suitable substituent(s) such as halogen (e.g., chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl, etc.), aryl (e.g., phenyl, tolyl, etc.), or the like.

Suitable lower alkyl and lower alkyl moiety in the terms "acyloxy(lower)alkyl", "acylthio(lower)alkyl" and "heterocyclicthio(lower)alkyl" may include one having 1 to 6 carbon atom(s), such as methyl, ethyl, propyl, isopropyl, butyl, isobutyl, tert-butyl, pentyl, tert-pentyl, hexyl or the like, preferably one having 1 to 3 carbon atoms(s).

Suitable protected carboxy may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.), wherein lower alkyl moiety may be preferably one having 1 to 4 carbon atom(s); lower alkenyl ester (e.g., vinyl ester, allyl ester, etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g., mesylmethyl ester, 2-mesylethyl ester, etc.); ar(lower)alkyl ester, for example, phenyl(lower)alkyl ester which may be substituted with one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); aryl ester which may have one or more suitable substituent(s) (e.g., phenyl ester, tolyl ester, tertiarybutylphenyl ester, xylyl ester, mesityl ester, cumenyl ester, etc.), and the like.

Preferable example of protected carboxy may be lower alkoxycarbonyl (e.g., methoxycarbonyl, ethoxycarbonyl, propoxycarbonyl, butoxycarbonyl, t-butoxycarbonyl, t-pentyloxycarbonyl, hexyloxycarbonyl, etc.) having 2 to 7 carbon atoms, preferably one having 2 to 5 carbon atoms and phenyl(lower)alkoxycarbonyl which may be substituted with nitro (e.g., 4-nitrobenzyloxycarbonyl, benzyloxycarbonyl, 4-nitrophenethyloxycarbonyl, etc.).

Suitable heterocyclic group and heterocyclic moiety in the term "a heterocyclicthio(lower)alkyl" means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; saturated 3 to 8-membered heteromonocyclic group containing 1 to 4 nitrogen atom(s), for example, pyrrolidinyl, imidazolidinyl, piperidino, piperazinyl, etc.; unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl, dihydrotriazolopyridazinyl, etc.; unsaturated 3- to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.; saturated 3 to 8-membered heteromonocyclic group containing 1 to 2 oxygen atom(s) and 1 to 3 nitrogen atom(s), for example, morpholinyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered heteromonocyclic group containing 1 to 2 sulfur atom(s) and 1 to 3 nitrogen atom(s), for example, thiazolyl, thiazolinyl, thiadiazolyl (e.g., 1,2,4-thiadiazolyl, 1,3,4-thiadiazolyl, 1,2,5-thiadiazolyl, etc.), etc.; saturated 3 to 8-membered heteromonocyclic group containing 1 to 2 sulfur atom(s) and 1 to 3 nitrogen atom(s), for example, thiazolidinyl, etc.; unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc. and the like;

wherein said heterocyclic group may be substituted with one or two suitable substituent(s) such as lower alkyl (e.g., methyl, ethyl, propyl, isopropyl, butyl, isobutyl, pentyl, hexyl, etc.), preferably one having 1 to 3 carbon atom(s); lower alkylthio (e.g., methylthio, ethylthio, propylthio, etc.); lower alkenyl (e.g., vinyl, allyl, butenyl, etc.), preferably one having 2 to 3 carbon atoms; lower alkenylthio (e.g., vinylthio, allylthio, butenylthio, etc.), preferably one having 2 to 3 carbon atoms; aryl (e.g., phenyl, tolyl, etc.); halogen (e.g., chlorine, bromine, iodine or fluorine); amino; di(lower)alkylamino(lower)alkyl (e.g., dimethylaminomethyl, dimethylaminoethyl, dimethylaminopropyl, diethylaminopropyl, diethylaminobutyl, etc.); carboxy(lower)alkyl (e.g., carboxymethyl, carboxyethyl, carboxypropyl, etc.), preferably one having 2 to 4 carbon atoms; esterified carboxy(lower)alkyl wherein the esterified carboxy moiety is exemplified above; amino(lower)alkyl (e.g., aminomethyl, aminoethyl, aminopropyl, 1-aminomethylethyl, aminobutyl, etc.), preferably one having 1 to 3 carbon atom(s); protected amino(lower)alkyl wherein the protected amino and lower alkyl moieties are each as exemplified above, preferably lower alkoxycarbonylamino(lower)alkyl (e.g., methoxycarbonylaminomethyl, ethoxycarbonylaminomethyl, t-butoxycarbonylaminomethyl, t-butoxycarbonylaminoethyl, t-butoxycarbonylaminopropyl, 1-t-butoxycarbonylaminomethylethyl, etc.), more preferably one having 3 to 9 carbon atoms, or lower alkanoylamino(lower)alkyl (e.g., acetylaminomethyl, acetylaminoethyl, acetylaminopropyl, 1-acetylaminomethylethyl, etc.), more preferably one having 2 to 5 carbon atoms; carboxy; esterified carboxy as exemplified above, preferably lower alkoxycarbonyl, more preferably one having 2 to 3 carbon atoms; lower alkoxy(lower)alkyl (e.g., methoxymethyl, methoxyethyl, methoxypropyl, ethoxymethyl, ethoxyethyl, etc.), preferably one having 2 to 5 carbon atoms; hydroxy(lower)alkyl(e.g., hydroxymethyl, hydroxyethyl, hydroxypropyl, hydroxybutyl, etc.), preferably one having 1 to 3 carbon atom(s); lower alkylthio(lower)alkyl (e.g., methylthiomethyl, methylthioethyl, methylthiopropyl, ethylthiomethyl, etc.), preferably one having 2 to 3 carbon atoms; sulfo(lower)alkyl (e.g., sulfomethyl, sulfoethyl, sulfopropyl, sulfobutyl, etc.), preferably one having 1 to 2 carbon atom(s); acyl(lower)alkyl wherein the acyl and lower alkyl moieties are each as exemplified above, preferably lower alkanesulfonyl(lower)alkyl (e.g., mesylmethyl, mesylethyl, ethanesulfonylmethyl, etc.), more preferably one having 2 to 3 carbon atoms; acylamino(lower)alkyl wherein the acyl and lower alkyl moieties are each as exemplified above, preferably lower alkanesulfonylamino(lower)alkyl (e.g., mesylaminomethyl, mesylaminoethyl, mesylaminopropyl, ethanesulfonylaminomethyl, etc.), more preferably one having 2 to 3 carbon atoms; carboxy(lower)alkylthio (e.g., carboxymethylthio, carboxyethylthio, etc.), preferably one having 2 to 3 carbon atoms; oxo; halo(lower)alkyl (e.g., chloromethyl, chloroethyl, dichloroethyl, trichloroethyl, trifluoromethyl, trichloromethyl, trifluoroethyl, etc.), preferably trihalo(lower)alkyl, more preferably one having 1 to 2 carbon atom(s); lower alkylamino (e.g., methylamino, ethylamino, propylamino, isopropylamino, etc.), preferably one having 1 to 2 carbon atom(s); protected amino as exemplified above; or the like.

Suitable lower alkylene may include straight or branched bivalent aliphatic hydrocarbon residue having 1 to 6 carbon atom(s), such as methylene, ethylene, methylethylene, propylene, trimethylene, 2-methyltrimethylene or the like, and preferably one having 1 to 4 carbon atom(s), more preferably one having 1 to 2 carbon atom(s) and the most preferably one having 1 carbon atom.

Suitable protected amino(lower)alkyl, protected amino and amino(lower)alkyl being the substituent of a heterocyclicthio(lower)alkyl for $R^{4c}$ and $R^{4d}$ can be each referred to the ones as exemplified above.

Suitable protective group of carboxy may be referred to the ones exemplified as aforementioned ester moiety in the esterified carboxy group. Preferable example of protective group of carboxy may be lower alkyl as mentioned above.

Suitable alkali metal may include sodium, potassium, lithium, etc.

Preferred embodiments of the object compound (I) are as follows.

Preferred embodiment of $R^1$ is amino, acylamino (more preferably lower alkanoylamino), di(lower)alkylamino(lower)alkylideneamino or phosphonoamino;

$R^2$ is lower alkyl;

$R^3$ is hydrogen or lower alkyl;

$R^4$ is hydrogen; acyloxy(lower)alkyl [more preferably lower alkanoyloxy(lower)alkyl or carbamoyloxy(lower)alkyl, most preferably lower alkanoyloxymethyl or carbamoyloxymethyl]; acylthio(lower)alkyl [more preferably lower alkanoylthio(lower)alkyl, most preferably lower alkanoylthiomethyl]; tetrazolylthio(lower)alkyl (more preferably tetrazolylthiomethyl) substituted with lower alkyl, lower alkenyl, lower alkoxy(lower)alkyl, lower alkylthio(lower)alkyl, hydroxy(lower)alkyl, amino(lower)alkyl, lower alkoxycarbonylamino(lower)alkyl, lower alkanoylamino(lower)alkyl, di(lower)alkylamino(lower)alkyl, sulfo(lower)alkyl or carboxy(lower)alkyl; thiadiazolylthio(lower)alkyl (more preferably thiadiazolylthiomethyl) which may be substituted with lower alkyl, lower alkoxy(lower)alkyl, lower alkylthio(lower)alkyl, lower alkenylthio, carboxy, lower alkoxycarbonyl, hydroxy(lower)alkyl, amino(lower)alkyl, lower alkoxycarbonylamino(lower)alkyl, amino, lower alkylamino, halo(lower)alkyl, carboxy(lower)alkylthio, lower alkanesulfonyl(lower)alkyl, lower alkanesulfonylamino(lower)alkyl or carboxy(lower)alkylthio; triazolylthio(lower)alkyl (more preferably triazolylthiomethyl)substituted with lower alkyl, lower alkenyl or lower alkoxy(lower)alkyl; pyrazinylthio(lower)alkyl (more preferably pyrazinylthiomethyl); thiazolinylthio(lower)alkyl(more preferably thiazolinylthiomethyl); tetrazolopyridazinylthio(lower)alkyl (more preferably tetrazolopyridazinylthiomethyl); or dihydrotriazolopyridazinylthio(lower)alkyl (more preferably dihydrotriazolopyridazinylthiomethyl) substituted with oxo and carboxy(lower)alkyl;

and $R^5$ is carboxy or phenyl(lower)alkoxycarbonyl substituted with nitro.

The processes for preparing the object compounds are explained in details in the following.

PROCESS 1

The object compound (I) can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include conventional reactive derivative used in amidation, for example, Schiff's base type imino or its tautomeric enamine type isomer formed by the reaction of the compound (II) with a carbonyl compound; a silyl derivative formed by the reaction of the compound (II) with a silyl compound such as bis(trimethylsilyl)acetamide, trimethylsilylacetamide or the like; a derivative formed by reaction of the compound (II) with phosphorus trichloride or phosgene, and the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, acetic acid or trichloroacetic acid, etc.) or aromatic carboxylic acid (e.g., benzoic acid, etc.); a symmetrical acid anhydride; an activated amide with imidazole, dimethylpyrazole, triazole or tetrazole; or an activated ester (e.g., cyanomethyl ester, methoxymethyl ester, dimethyliminomethyl [$(CH_3)_2N^+=CH-$]ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (III) to be used.

The salts of the compound (III) may be salts with an inorganic base such as an alkali metal salts (e.g., sodium or potassium salt), or an alkaline earth metal salt (e.g., calcium or magnesium salt), a salt with an organic base such as trimethylamine, triethylamine, pyridine, a salt with an acid (e.g., hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the compound (III) is used in free acid form or its salt form in the reaction, the reaction is preferably carried out in the presence of a conventional condensing agent such as N,N-dicyclohexylcarbodiimide; N-cyclohexyl-N'-morpholinoethylcarbodiimide; N-cyclohexyl-N'-(4-diethylaminocyclohexyl)carbodiimide; N,N-diethylcarbodiimide; N,N-diisopropylcarbodiimide; N-ethyl-N'-(3-dimethylaminopropyl)carbodiimide; N,N-carbonylbis(2-methylimidazole); pentamethylene-ketene-N-cyclohexylimine; diphenylketene-N-cyclohexylimine; ethoxyacetylene; ethyl polyphosphate; isopropyl polyphosphate; diethyl phosphorochloridite; phosphorus oxychloride; phosphorous trichloride; phosphorus pentachloride; thionyl chloride; oxalyl chloride; triphenylphosphine; N-ethyl-7-hydroxybenzisoxazolium fluoroborate; N-ethyl-5-phenylisoxazolium-3'-sulfonate; 1-(p-chlorobenzenesulfonyloxy)-6-chloro-1H-benzotriazole; so-called Vilsmeier reagent, for example (chloromethylene)dimethylammonium chloride produced by the reaction of dimethylformamide with thionyl chloride or phosgene, a compound produced by the reaction of dimethylformamide with phosphorus oxychloride, etc.; or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorpholine, N,N-di(lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, a syn-isomer of the object compound (I) can be obtained preferably by conducting the reaction of the compound (II) with a synisomer of the starting compound (III).

In the present reaction, amino group for $R^1$ in the compound (III) may be converted into a protected amino group to give the compound (I) wherein $R^1$ is a protected amino in the course of the reaction according to reaction conditions, and this case is also included within the scope of the present reaction.

PROCESS 2

The object compound (Ib) or a salt thereof can be prepared by subjecting the compound (Ia) or a salt thereof to elimination reaction of the protective group of carboxy.

Suitable salt of the compound (Ia) can be referred to the acid addition salt exemplified for the compound (II).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]none-5-ene, 1,4-diazabicyclo[2,2,2]octane, 1,8-diazabicyclo[5,4,0]undecene-7, or the like. Suitable acid may include an organic acid (e.g., formic acid, acetic acid, propionic acid, trifluoroacetic acid, etc.) and an inorganic acid (e.g., hydrochloric acid, hydrobromic acid, sulfuric acid, etc.).

The reaction is usually carried out in a solvent such as water, an alcohol (e.g., methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g., zinc, zinc amalgam, etc.) or a salt of chrome compound (e.g., chromous chloride, chromous acetate, etc.) and an organic or inorganic acid (e.g., acetic acid, propionic acid, hydrochloric acid, etc.); and conventional catalytic reduction in the presence of a conventional metallic catalyst (e.g., palladium-carbon, etc.).

PROCESS 3

The object compound (Id) or a salt thereof can be prepared by reacting the compound (Ic) or a salt thereof with the compound (IV) or its reactive derivative at the mercapto group.

Suitable salt of the compound (Ic) can be referred to the ones exemplified for the compound (II).

Suitable reactive derivative at the mercapto group of the compound (IV) may include a metal salt such as an alkali metal salt (e.g., sodium salt, potassium salt, etc.) or the like.

The present reaction may be carried out in a solvent such as water, phosphate buffer, acetone, chloroform, nitrobenzene, methylene chloride, ethylene chloride, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (Ic) or the compound (IV) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under slightly heating.

PROCESS 4

The object compound (If) or a salt thereof can be prepared by subjecting the compound (Ie) or a salt thereof to elimination reaction of the protective group of amino.

Suitable salt of the compound (Ie) may include a metal salt, ammonium salt, an organic amine salt and the like as aforementioned.

The present elimination reaction is carried out in accordance with a conventional method such as hydrolysis; reduction; a method by reacting the compound (Ie) wherein the pretective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g., t-pentyloxycarbonyl, t-butoxycarbonyl, etc.), alkanoyl (e.g., formyl, etc.), cycloalkoxycarbonyl, substituted or unsubstituted aralkoxycarboxyl (e.g., benzyloxycarbonyl, substituted benzyloxycarbonyl, etc.), substituted phenylthio, substituted aralkylidene, substituted alkylidene, substituted cycloalkylidene, ar(lower)alkyl (e.g., benzyl, trityl, etc.) or the like.

Suitable acid may include an organic or an inorganic acid, for example, formic acid, trifluoroacetic acid, benzenesulfonic acid, p-toluenesulfonic acid, hydrochloric acid and the like, and preferable acid is, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent, water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g., dichloroacetyl, trifluoroacetyl, etc.) etc. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1-4-diazabicyclo[2,2,2]octane, 1,5-diazabicyclo[5,4,0]undecene-5- or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g., trichloroethoxycarbonyl etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g., sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present reaction includes, within its scope, the cases that the protected carboxy group for $R^5$ is transformed into the free carboxy group in the course of the elimination reaction as mentioned above or in the post-treatment of the reaction mixture or reaction product.

The preparation for preparing the starting compound (III) are explained below in detail.

PREPARATION (1)

The compound (VII) can be prepared by reacting the compound (V) or a salt thereof with halogenating agent and the compound (VI).

Suitable halogenating agent to be used in the present reaction may include bromine, chlorine and the like.

The present reaction is preferably carried out in the presence of a base such as an inorganic base or an organic base, for example, alkali metal carbonate, alkali metal alkoxide, trialkylamine or the like. The present reaction is usually carried out in a solvent such as an alcohol (e.g., methanol, ethanol, etc.) or any other solvent which does not adversely affect the reaction. The reaction temperature is not critical and the reaction is usually carried out under cooling or at ambient temperature. In this reaction, $R^6$ of the compound (V) may be converted into other protective group of carboxy according to reaction conditions and kinds of the protective group and it is included within the scope of the present reaction.

PREPARATION (2)

The compound (VIII) can be prepared by subjecting the compound (VII) to introduction reaction of the protective group of amino.

The present process can be carried out in a conventional manner and when the protective group of amino to be introduced into the amino group is acyl, the reaction can be carried out in substantially the same manner as that of Process 1. Accordingly, the detailed explanation therefor is to be referred to said Process 1.

PREPARATION (3)

The compound (X) can be prepared by reacting the compound (VIII) with the compound (IX). This process is usually carried out in the presence of base such as an alkali metal hydride (e.g., sodium hydride, potassium hydride, etc.), an alkaline earth metal hydride (e.g., calcium hydride, etc.) and the like, and usually carried out in a solvent such as dimethylformamide or any other solvent which does not adversely affect the reaction. The reaction temperature is not critical and the reaction is usually carried out under cooling, at ambient temperature or under warming.

PREPARATION (4)

The compound (XI) can be prepared by reacting the compound (X) with an acid and/or acid anhydride such as acetic acid and/or acetic anhydride. The reaction of this process can preferably be carried out in the presence of alkali metal perhaloate (e.g., sodium perchlorate, sodium periodate, potassium perchlorate, etc.), alkaline earth metal perchlorate (e.g., magnesium perchlorate, calcium perchlorate, etc.) and the like, and an acid such as an organic acid (e.g., formic acid, acetic acid etc.) or an inorganic acid (e.g., hydrochloric acid).

The reaction temperature is not critical and the reaction is usually carried out under warming.

PREPARATIONS (5) and (7)

The preparation (5) and (7) can be carried out in a conventional manner as shown in Process 2 or 4.

In the preparation (5), according to reaction conditions, there may be obtained the product having $R^{1a}$ or the product having amino group instead of $R^{1a}$, and they are subsequently reacted with the compound (XII) or a salt thereof to give the compound (IIIa) or (IIIb), respectively, as shown in Preparation (6).

PREPARATION (6)

Suitable salt of the compound (XII) is a conventional acid salt such as an inorganic acid salt (e.g., hydrochloride, etc.) and an organic acid salt (e.g., p-toluenesulfonic acid salt, etc). When salt of said compound (XII) is used in this process, the reaction is usually carried out in the presence of a base such as an alkali metal hydroxide (e.g., sodium hydroxide, potassium hydroxide, etc.). The reaction is usually carried out in a solvent such as water, an alcohol (e.g., methanol, ethanol, etc.) or any other solvent which does not adversely affect the reaction. The reaction temperature is not critical and the reaction is usually carried out at ambient temperature.

In the aforementioned reactions and/or in the post treatment of the reactions of the present invention, the aforementioned tautomeric isomers may occasionally be transformed into the other tautomeric isomers and such case is also included in the scope of the present invention.

In case that the object compound (I) is obtained in a form of the free acid at 4 position and/or in case that the object compound (I) has free amino group, it may be optionally transformed into its pharmaceutically acceptable salt as aforementioned by a conventional method.

The object compound (I) and pharmaceutically acceptable salt thereof of the present invention are all novel compounds which exhibit high antibacterial activity, inhibiting the growth of a wide variety of pathogenic microorganisms including Gram-positive and Gram-negative bacteria and are useful as antibacterial agents.

Now, in order to show the utility of the object compound (I), with regard to some representative compounds of this invention, the test data on the in vitro anti-bacterial activity are shown in the following.

TEST COMPOUNDS (1) 7-[2-Methoxyimino-2-(5-amino-1,2,4-thiadiazol-3-yl)acetamido]-3-(1-methyl-1H-tetrazol-5-ylthiomethyl)-3-cephem-4-carboxylic acid (syn isomer)

(2) 7-[2-Methoxyimino-2-(5-amino-1,2,4-thiadiazol-3-yl)acetamido]-3-(1,3,4-thiadiazol-2-ylthiomethyl)-3-cephem-4-carboxylic acid (syn isomer)

(3) 7-[2-Methoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer)

(4) 7-[2-Ethoxyimino-2-(5-amino-1,2,4-thiadiazol-3-yl)acetamido]-3-(1,3,4-thiadiazol-2-yl)thiomethyl-3-cephem-4-carboxylic acid (syn isomer)

(5) 7-[2-Methoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer)

(6) 7-[2-Methoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer)

(7) 7-[2-Isopropoxyimino-2-(5-amino-1,2,4-thiadiazol-3-yl)acetamido]-3-(1,3,4-thiadiazol-2-yl)thiomethyl-3-cephem-4-carboxylic acid (syn isomer)

(8) 7-[2-Methoxyimino-2-(5-amino-1,2,4-thiadiazol-3-yl)acetamido]-3-(1-allyl-1H-tetrazol-5-yl)thiomethyl-3-cephem-4-carboxylic acid (syn isomer)

(9) 7-[2-Ethoxyimino-2-(5-amino-1,2,4-thiadiazol-3-yl)acetamido]-3-cephem-4-carboxylic acid (syn isomer)

(10) 7-[2-Methoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer)

TEST METHOD

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of test compounds, and minimal inhibitory concentration (MIC) was expressed in terms of $\mu$g/ml. after incubation at 37° C. for 20 hours.

| Test Bacteria | Test Results MIC (μg/ml) Test Compound | | | | | | | | | |
|---|---|---|---|---|---|---|---|---|---|---|
| | (1) | (2) | (3) | (4) | (5) | (6) | (7) | (8) | (9) | (10) |
| B. subtilis ATCC 6633 | 3.13 | 3.13 | 6.25 | 3.13 | 6.25 | 3.13 | 1.56 | 3.13 | 12.5 | 6.25 |
| E. coli NIHJ JC-2 | 0.2 | 0.05 | 0.2 | 0.2 | 0.1 | 0.1 | 0.78 | 0.1 | 0.05 | 0.1 |
| Kl. pneumoniae 12 | 0.2 | 0.1 | 0.1 | 0.39 | 0.05 | 0.39 | 3.13 | 0.39 | 0.2 | 0.2 |
| Pr. vulgaris 2 | 0.2 | 0.2 | 0.1 | 0.2 | 0.05 | 0.2 | 0.39 | 0.39 | 0.05 | 0.78 |
| Ps. aeruginosa NCTC-10490 | 6.25 | 3.13 | 6.25 | 3.13 | 12.5 | 12.5 | 3.13 | 6.25 | 3.13 | 12.5 |

For therapeutic administration, the object compound (I) of the present invention is used in the form of conventional pharmaceutical preparation which contains said compounds, as an active ingredient, in admixture with a pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc., an average single dose of about 50 mg., 100 mg., 250 mg, and 500 mg. of the object compound (I) of the present invention has proved to be effective in treating diseases infected by pathogenic bacteria.

In general, daily dose between 5 mg. and about 3,000 mg. or even more may be administered to a patient.

The following preparations and examples are given for the purpose of illustrating the present invention:

PREPARATION 1

Preparation of Methyl 5-amino-1,2,4-thiadiazole-3-carboxylate.

To a solution of 1-ethoxycarbonylformamidine. hydrobromide (16.6 g.) in absolute methanol (84 ml) was added a solution of sodium (1.93 g) in absolute methanol (42 ml) at 0° C. To the mixture were added alternately bromine (12.8 g) and a solution of sodium (1.93 g) in absolute methanol (42 ml) at 0° C. and then to the suspension was added potassium thiocyanate (8.1 g) in absolute methanol (100 ml). The reaction mixture was stirred for an hour at 0° C. and for an additional 6 hours at ambient temperature. The mixture was filtered through cellulose powder and the filtrate was evaporated to dryness. The residue was dissolved in a mixture of ethyl acetate and water, and then the ethyl acetate layer was separated and dried over anhydrous magnesium sulfate. The solvent was evaporated and the residue was triturated with diethyl ether to give the title compound (9.0 g), mp. 202° to 205° C.

I.R. (Nujol): 3400, 3250, 3100, 1710, 1610, 1540 cm$^{-1}$.

N.M.R. (d$_6$-DMSO) δ: 3.85 (3H, s), 8.25 (2H, s).

PREPARATION 2

Preparation of Methyl 5-formamido-1,2,4-thiadiazole-3-carboxylate.

To a mixture of formic acid (33 g) and acetic anhydride (22 g) was added methyl 5-amino-1,2,4-thiadiazole-3-carboxylate (6.2 g), and then the mixture was stirred for 2 days at ambient temperature. The reaction mixture was concentrated under reduced pressure and the residue was triturated with a mixture of diethyl ether and n-hexane to give the title compound (7.2 g), mp. 210° to 215° C.

I.R. (Nujol): 3100, 1720, 1680 cm$^{-1}$.

N.M.R. (d$_6$-DMSO) δ:3.90 (3H, s), 8.85 (1H, s).

PREPARATION 3

Preparation of 5-Formamido-3-(2-methylthio-2-methylsulfinylacetyl)-1,2,4-thiadiazole.

To a mixture of methyl 5-formamido-1,2,4-thiadiazole-3-carboxylate (9.2 g) and methyl methylthiomethyl sulfoxide (6.1 g) in N,N-dimethylformamide (100 ml) was added 50% sodium hydride (7.1 g) with cooling in an ice-bath. The mixture was stirred for an hour at ambient temperature and for an additional one hour at 40° C. After cooling to ambient temperature, methylene chloride (300 ml) was added to the reaction mixture, and the resulting precipitates were collected by filtration and washed with methylene chloride. The precipitates were added to a stirred mixture of hydrochloric acid (14.7 ml), ice-water (200 ml) and methylene chloride (200 ml). An insoluble material was filtered off and the methylene chloride layer was separated from the filtrate. The solution was dried over anhydrous magnesium sulfate, evaporated and the residue was triturated with diethyl ether to give the title compound (4.5 g), mp. 130° to 132° C.

I.R. (Nujol): 3100, 1680, 1670 cm$^{-1}$.

| N.M.R. (d$_6$-DMSO) δ: | | |
|---|---|---|
| 2.22 | } | (3H, 2s) |
| 2.28 | | |
| 2.68 | } | (2H, 2s) |
| 2.85 | | |
| 5.70 | } | (1H, 2s) |
| 5.80 | | |
| 8.86 | | (1H, s) |

PREPARATION 4

Preparation of S-methyl (5-formamido-1,2,4-thiadiazol-3-yl)thioglyoxylate.

A mixture of 5-formamido-3-(2-methylthio-2-methylsulfinylacetyl)-1,2,4-thiadiazole (0.85 g) and sodium periodate (0.2 g) in glacial acetic acid (10 ml) was stirred for 45 minutes at 70° C. The reaction mixture was evaporated and the residue was dissolved in a mixture of ethyl acetate and water. The mixture was adjusted to pH 7 with an aqueous solution of sodium bicarbonate and treated with an aqueous solution of sodium thiosulfate. The organic layer was separated, dried over anhydrous magnesium sulfate and evaporated to dryness. The residue was triturated with a mixture of diethyl ether and petroleum ether to give the title compound (280 mg), mp. 186° to 187° C.

I.R. (Nujol): 3100, 1680, 1660 cm$^{-1}$.

N.M.R. (d$_6$-DMSO) δ: 2.55 (3H, s), 8.95 (1H, s).

PREPARATION 5

Preparation of 2-Methoxyimino-2-(5-formamido-1,2,4-thiadiazol-3-yl)acetic acid (syn isomer).

A mixture of S-methyl (5-formamido-1,2,4-thiadiazol-3-yl)thioglyoxylate (231 mg) in methanol (2 ml) and 1N-aqueous solution of potassium hydroxide (3.5 ml) was stirred for an hour at ambient temperature. The mixture was adjusted to pH 7.6 with 1N hydrochloric acid, followed by an addition of O-methylhydroxylamine hydrochloride (90 mg) and stirring for 30 minutes at ambient temperature. The reaction mixture was neutralized with an aqueous solution of sodium bicarbonate and concentrated to remove methanol. The concentrated aqueous solution was adjusted to pH 4 with hydrochloric acid and washed with ethyl acetate. The aqueous layer was adjusted to pH 1 with hydrochloric acid, saturated with sodium chloride and extracted with ethyl acetate. The extract was evaporated to dryness and the residue was triturated with diethyl ether, collected by filtration and then dried to give the title compound (80mg), mp. 185° to 186° C.

I.R. (Nujol): 3150, 1720, 1690 cm$^{-1}$.

N.M.R. (d$_6$-DMSO) δ: 3.98 (3H, s), 8.84 (1H, s).

PREPARATION 6

Preparation of 2-Methoxyimino-2-(5-formamido-1,2,4-thiadiazol-3-yl)acetic acid (syn isomer).

A mixture of 5-formamido-3-(2-methylthio-2-methylsulfinylacetyl)-1,2,4-thiadiazol (3.2 g) and sodium periodate (0.8 g) in glacial acetic acid (32 ml) was stirred for 45 minutes at 70° C. The resulting mixture was evaporated and the residue was washed with n-hexane and then thereto were added methanol (20 ml) and 1N aqueous solution of potassium hydroxide (40 ml). The solution was stirred for an hour at ambient temperature. The reaction mixture was adjusted to pH 8 with 1N hydrochloric acid, followed by an addition of O-methylhydroxylamine hydrochloride (0.96 g) and stirring for an hour at ambient temperature. The reaction mixture was neutralized with an aqueous solution of sodium bicarbonate and concentrated to remove methanol. The resulting aqueous solution was washed with ethyl acetate, adjusted to pH 1 with 10% hydrochloric acid, saturated with sodium chloride and extracted with ethyl acetate. The extract was dried over anhydrous magnesium sulfate, evaporated, and the residue was triturated with diisopropyl ether to give the title compound (1.02 g), mp. 185° to 186° C.

PREPARATION 7

Preparation of 2-Methoxyimino-2-(5-amino-1,2,4-thiadiazol-3-yl)acetic acid (syn isomer).

A solution of 2-methoxyimino-2-(5-formamido-1,2,4-thiadiazol-3-yl)acetic acid (syn isomer) (1.4 g) in 1N aqueous solution of sodium hydroxide (19.1 ml) was heated at 50° to 55° C. for an hour. To the solution was added conc.hydrochloric acid (1.9 ml) under cooling in an ice-bath. The mixture was saturated with sodium chloride and extracted with ethyl acetate. The extract was dried over anhydrous magnesium sulfate and evaporated to dryness. The residue was triturated with diethyl ether to give the title compound (0.9 g), mp. 180° to 182° C. (dec.).

I.R. (Nujol): 3450, 3250, 3100, 1715, 1610, 1530 cm$^{-1}$.

N.M.R. (d$_6$-DMSO) δ: 3.90 (3H, s), 8.10 (3H, broad s).

PREPARATION 8

A mixture of 5-formamido-3-(2-methylthio-2-methylsulfinylacetyl)-1,2,4-thiadiazole (10 g) and sodium periodate (2.0 g) in glacial acetic acid (50 ml) was stirred for 50 minutes at 70° C. The solvent was evaporated and the residue was washed with n-hexane. To the residue was added 1N aqueous solution of sodium hydroxide (160 ml) and the mixture was stirred for an hour at ambient temperature. To the reaction mixture was added O-ethylhydroxylamine hydrochloride (3.5 g) and the solution was adjusted to pH 3 to 4 with 10% hydrochloric acid and then stirred for an hour at ambient temperature. After an insoluble material was filtered off, the filtrate was washed with ethyl acetate, adjusted to pH 1 with 10% hydrochloric acid and extracted with ethyl acetate. The extract was dried over magnesium sulfate and evaporated to dryness. The residue was triturated with a mixture of diethyl ether and diisopropyl ether to give 2-ethoxyimino-2-(5-formamido-1,2,4-thiadiazol-3-yl)acetic acid (syn isomer) (4.5 g), mp 165° to 168° C. (dec.).

I.R. (Nujol): 3450, 3170, 3050, 1730, 1690, 1595, 1565 cm$^{-1}$.

N.M.R. (d$_6$-DMSO) δ: 1.30 (3H, t, J=7 Hz), 4.30 (2H, q, J=7 Hz), 8.87 (1H, s).

PREPARATION 9

The following compounds were obtained according to a similar manner to that of Preparation 8.

(1) 2-Propoxyimino-2-(5-formamido-1,2,4-thiadiazol-3-yl)acetic acid (syn isomer), mp. 168° to 170° C. (dec.).

I.R. (Nujol): 3250, 3140, 1720, 1690, 1590, 1530 cm$^{-1}$.

N.M.R. (d$_6$-DMSO) δ: 0.90 (3H, t, J=6 Hz), 1.4-1.9 (2H, m), 4.17 (2H, t, J=6 Hz), 8.85 (1H, s).

(2) 2-Isopropoxyimino-2-(5-formamido-1,2,4-thiadiazol-3-yl)acetic acid (syn isomer), mp 180° to 182° C. (dec.).

I.R. (Nujol): 3230, 1720, 1690, 1590, 1530 cm$^{-1}$.

N.M.R. (d$_6$-DMSO) δ: 1.25 (6H, d, J=6 Hz), 4.2-4.7 (1H, m), 8.85 (1H, s).

PREPARATION 10

A mixture of 2-ethoxyimino-2-(5-formamido-1,2,4-thiadiazol-3-yl)acetic acid (syn isomer) (4.4 g) and 1N aqueous solution of sodium hydroxide (54 ml) was stirred for 2 hours at 50° to 55° C. The mixture was cooled in an ice bath, acidified with hydrochloric acid (5.4 ml) and extracred with ethyl acetate. The extract was dried over magnesium sulfate and evaporated to dryness. The residue was triturated with diethyl ether to give 2-ethoxyimino-2-(5-amino-1,2,4-thiadiazol-3-yl)acetic acid (syn isomer) (2.92 g), mp. 168° to 170° C. (dec.).

I.R. (Nujol): 3450, 3370, 3250, 3150, 1665, 1610, 1530 cm$^{-1}$.

N.M.R. (d$_6$-DMSO) δ: 1.22 (3H, t, J=7 Hz), 4.17 (2H, q, J=7 Hz), 8.17 (2H, broad s).

PREPARATION 11

The following compounds were obtained according to a similar manner to that of Preparation 10.

(1) 2-Propoxyimino-2-(5-amino-1,2,4-thiadiazol-3-yl)acetic acid (syn isomer), mp. 100° to 103° C. (dec.).

I.R. (Nujol): 3620, 3520, 3350, 3120, 2600, 2500, 1720, 1620, 1550 cm$^{-1}$.

N.M.R. (d$_6$-DMSO) δ: 1.00 (3H, t, J=6 Hz), 1.3-2.0 (2H, m), 4.13 (2H, t, J=6 Hz), 8.17 (2H, broad, s).

(2) 2-Isopropoxyimino-2-(5-amino-1,2,4-thiadiazol-3-yl)acetic acid (syn isomer), mp. 152° to 155° C. (dec.).

I.R. (Nujol): 3450, 3300, 3200, 1730, 1620, 1530 cm$^{-1}$.

N.M.R. (d$_6$-DMSO) δ: 1.22 (6H, d, J=6 Hz), 4.1-4.6 (1H, m), 8.20 (2H, broad s).

PREPARATION 12

A mixture of 7-aminocephalosporanic acid (14.31 g), 5-allylthio-1,3,4-thiadiazole-2-thiol (14 g), sodium bicarbonate (10.6 g), water (33 ml) and pH 6.4 phosphate buffer solution (105 ml) was stirred for 4 hours at 65° to 70° C. To the reaction mixture was added ethyl acetate (50 ml) and the mixture was adjusted to pH 3 with hydrochloric acid. Precipitates were collected by filtration, washed with water, methanol and acetone, and dried to give pale brown powder of crude 7-amino-3-(5-allylthio-1,3,4-thiadiazol-2-yl)thiomethyl-3-cephem-4-carboxylic acid (13.4 g). Said powder (10 g) was dissolved in a mixture of methanol (100 ml) and conc.hydrochloric acid (70 ml) and filtered. The filtrate was treated with an activated charcoal and adjusted to pH 3 with aqueous ammonia. Ethyl acetate (50 ml) was added thereto and precipitates were collected by filtration, washed with water and acetone, and dried to give pure object compound (5.2 g), mp 195° to 197° C.

I.R. (Nujol): 3150, 2700-2500, 1800, 1610, 1550-1510, 1040, 720 cm$^{-1}$.

PREPARATION 13

(1) A solution of methyl N-(3-methoxypropyl)-dithiocarbamate (100.2 g) in ethanol (300 ml) was added dropwise at 3° C. over 30 minutes to a solution of hydrazine hydrate (28 g) in ethanol (200 ml). The mixture was stirred for 4.5 hours at 70° C. The reaction mixture was concentrated and to the residue were added water and diethyl ether. The diethyl ether extract was dried over magnesium sulfate and evaporated in vacuo to give pinkish oil of 4-(3-methoxypropyl)thiosemicarbazide (89.9 g).

N.M.R. (CDCl$_3$) δ: 1.87 (2H, m), 3.33 (3H, s), 3.3-3.8 (4H, m), 4.0 (2H, broad s), 7.8 (1H, broad s).

(2) A mixture of 4-(3-methoxypropyl)thiosemicarbazide (89.9 g) and formic acid (450 ml) was refluxed with stirring for 8.5 hours at 105° C. Formic acid was removed in vacuo from the reaction mixture and to the residue were added ethyl acetate (800 ml) and water (200 ml). The separated organic layer was washed with 5% aqueous solution of sodium bicarbonate and with an aqueous solution of sodium chloride, dried over magnesium sulfate and concentrated to give orange oil (77.52 g). To the oil were added a solution of sodium hydroxide (26 g) in water (260 ml) and methanol (40 ml), and then methanol was distilled off under reduced pressure. To the residue was added water (100 ml), and the mixture was adjusted to pH 3 or 4 with 10% hydrochloric acid and extracted with ethyl acetate (150 ml×2). The extracts were dried over magnesium sulfate and evaporated to give orange oil (40.32 g). The oil was purified by column chromatography on silica gel (500 g) using ethyl acetate as eluent to give oil of 4-(3-methoxypropyl)-4H-1,2,4-triazole-3-thiol (8.95 g).

N.M.R. (CDCl$_3$) δ: 2.14 (2H, m), 3.40 (3H, s), 3.47 (2H, t, J=7 Hz), 4.18 (2H, t, J=7 Hz), 7.94 (1H, s).

PREPARATION 14

(1) A solution of N-(3-aminopropyl)acetamide (146 g) in dioxane (710 ml) was added to a solution of 97% sodium hydroxide (52 g) in water (620 ml) and then carbon disulfide (96 g) was added dropwise thereto over 35 minutes at −1° to 3° C. The mixture was stirred for 1 hour at 0° to 2° C. To the mixture containing sodium N-(3-acetamidopropyl)dithiocarbamate was added dropwise methyl iodide (179 g) over 35 minutes at 0° to 5° C. and then the resulting mixture was stirred for 3 hours at the same temperature. Dioxane was distilled off in vacuo from the reaction mixture and the residue was extracted with ethyl acetate (300 ml, 200 ml×4). The extracts were dried over magnesium sulfate and concentrated in vacuo to give oil of methyl N-(3-acetamidopropyl)dithiocarbamate (193.18 g).

(2) A mixture of a solution of methyl N-(3-acetamidopropyl)dithiocarbamate (193 g) in dioxane (610 ml) and a solution of sodium azide (79.42 g) in water (500 ml) was refluxed under stirring for 4 hours. Dioxane was distilled off and the remaining aqueous layer was washed with diethyl ether (150 ml×2), adjusted to pH 1 with 17.5% hydrochloric acid, and cooled in an ice bath. Precipitates were collected by filtration and washed with ice-water to give white powder of 1-(3-acetamidopropyl)-1H-tetrazol-5-thiol (91.75 g), mp. 152° to 154° C.

N.M.R. (d$_6$-DMSO) δ: 1.87 (3H, s), 1.97 (2H, m), 3.17 (2H, m), 4.28 (2H, t, J=7 Hz), 7.9 (1H, broad s), 15.0 (1H, broad s).

(3) A mixture of 1-(3-acetamidopropyl)-1H-tetrazole-5-thiol (85 g) and 6N hydrochloric acid (1 l) was refluxed for 75 minutes under stirring. The reaction mixture was concentrated in vacuo and precipitates were collected by filtration and washed with hexane and diethyl ether to give 1-(3-aminopropyl)-1H-tetrazole-5-thiol hydrochloride (67.15 g).

N.M.R. (D$_2$O) δ: 2.45 (2H, m), 3.23 (2H, t, J=7 Hz), 4.50 (2H, t, J=7 Hz).

(4) A solution of 2-t-butoxycarbonyloxyimino-2-phenylacetonitrile (12.3 g) in dioxane (30 ml) was added under ice-cooling to a stirred solution of 1-(3-aminopropyl)-1H-tetrazole-5-thiol hydrochloride (9.78 g) and triethylamine (11.1 g) in a mixture of dioxane (25 ml) and water (25 ml), and then the resulting mixture was stirred for 1.75 hours at ambient temperature. Dioxane was distilled off and to the residue were added diethyl ether and a small amount of water. After shaking, the aqueous layer was separated and the organic layer was extracted twice with 10% potassium carbonate. The extracts combined with the separated aqueous layer were washed three times with diethyl ether, adjusted to pH 1 with hydrochloric acid and extracted with diethyl ether. The extract was washed with water, dried and evaporated in vacuo. The residual oil (10.92 g) was pulverized with diisopropyl ether to give 1-[3-(N-t-butoxycarbonylamino)propyl]-1H-tetrazole-5-thiol (9.6 g), mp. 75° to 77° C.

I.R. (Nujol): 3380, 3260, 1650, 1530, 1170, 1050 cm$^{-1}$.

N.M.R. (CDCl$_3$) δ: 1.50 (9H, s), 2.14 (2H, m), 3.25 (2H, m), 4.39 (2H, t, J=7 Hz), 4.9-6.7 (1H, broad).

PREPARATION 15

(1) To a mixture of methyl 5-amino-1,2,4-thiadiazole-3-carboxylate (26 g), conc.hydrochloric acid (490 ml) and a small amount of copper was added dropwise over 40 minutes a solution of sodium nitrite (22.5 g) in water (28 ml) at $-10°$ to $-15°$ C. The mixture was stirred for 1.5 hours at the same temperature and for 30 minutes at 50° C. The reaction mixture was poured into ice-water (500 ml) and extracted with ethyl acetate. The extract was washed, dried and concentrated to give white powder of methyl 5-chloro-1,2,4-thiadiazole-3-carboxylate (8.9 g).

I.R. (Nujol): 1730, 1430, 1385, 1320, 1220, 1065, 980, 830 cm$^{-1}$.

N.M.R. (CDCl$_3$) δ: 4.01 (3H, s).

(2) A mixture of methyl 5-chloro-1,2,4-thiadiazole-3-carboxylate (7.80 g), thiourea (3.32 g), tetrahydrofuran (24 ml) and water (8 ml) was gently boiled for 6.5 hours. The reaction mixture was post-treated according to conventional manner to give yellow powder to methyl 5-mercapto-1,2,4-thiadiazole-3-carboxylate (7.1 g), mp. 126° to 127° C.

I.R. (Nujol): 1730, 1430, 1360, 1270, 1060 cm$^{-1}$.

N.M.R. (d$_6$-DMSO) δ: 3.91 (3H, s), 9.33 (1H, m).

PREPARATION 16

(1) Trichloromethylsulfur monochloride (88.33 g) was added at 0° C. to a solution of 2-allylisothiourea hydrobromide (93.6 g) in water (285 ml) and then a solution of sodium hydroxide (76 g) in water (300 ml) was added dropwise thereto over 4 hours with stirring. After stirring for 1 hour, the reaction mixture was post-treated according to conventional manner to give reddish brown oil of 3-allylthio-5-chloro-1,2,4-thiadiazole (84 g), bp. 105° to 111° C./13 mmHg.

I.R. (Film): 1450, 1220, 1070 cm$^{-1}$.

N.M.R. (CDCl$_3$) δ: 3.90 (2H, d, J=6 Hz), 5.15–5.47 (2H, m), 5.67–6.34 (1H, m).

(2) A mixture of 3-allylthio-5-chloro-1,2,4-thiadiazole (15.0 g), thiourea (5.95 g), tetrahydrofuran (45 ml) and water (15 ml) was gently boiled for 8.5 hours at 65° C. The reaction mixture was post-treated according to conventional manner to give powder of 3-allylthio-1,2,4-thiadiazole-5-thiol (8.5 g), mp. 107° to 108° C.

I.R. (Nujol): 1510, 1430, 1170, 1095, 900 cm$^{-1}$.

PREPARATION 17

(1) A solution of N-(2-aminopropyl)acetamide (82.9 g) in dioxane (415 ml) was added to a solution of 97% sodium hydroxide (29.5 g) in water (330 ml). To the mixture was added dropwise at 0° to 5° C. over 25 minutes carbon disulfide (54.5 g), after which the mixture was stirred for 1 hour at 0° to 5° C. Methyl iodide (101.5 g) was added dropwise over 30 minutes at 0° to 3° C. to the resultant mixture and the mixture was stirred for 3 hours at the same temperature. The reaction mixture was concentrated and extracted with ethyl acetate (200 ml, 100 ml×2). The extracts were dried over magnesium sulfate and evaporated to give oil (164.2 g). The oil was subjected to column chromatography on silica gel (900 g) and successively eluted with a mixture of benzene and ethyl acetate (1:1) and ethyl acetate to give oil of a mixture of methyl N-(2-acetamidopropyl)dithiocarbamate and methyl N-[1-(acetamidomethyl)ethyl]-dithiocarbamate (114.1 g).

I.R. (Film): 3400–3200, 1730, 1670–1630, 1560–1500, 1310, 1280, 1250, 1150, 960 cm$^{-1}$.

(2) A mixture of methyl N-(2-acetamidopropyl)dithiocarbamate and methyl N-[1-(acetamidomethyl)ethyl]-dithiocarbamate (100 g) in dioxane (300 ml) and a solution of sodium azide (41 g) in water (270 ml) were stirred for 4.5 hours under reflux. The reaction mixture was concentrated to half volume under reduced pressure, washed with diethyl ether and acidified with concentrated hydrochloric acid. The resulting precipitate was collected by filtration and washed with diethyl ether to give pale yellow powder of 1-[1-(acetamidomethyl)ethyl]-1H-tetrazole-5-thiol (26.32 g), mp 176° to 178° C.

I.R. (Nujol): 3420, 2850, 1640, 1550, 1520, 1390, 1350, 1310, 1210, 1050, 990 cm$^{-1}$.

N.M.R. (d$_6$-DMSO,δ): 1.40 (3H, d, J=7 Hz), 1.75 (3H, s), 3.51 (2H, m), 4.91 (1H, m), 8.00 (1H, t, J=6 Hz).

(3) A mixture of 1-[1-(acetamidomethyl)ethyl]-1H-tetrazole-5-thiol (23 g) and 6N aqueous hydrochloric acid (300 ml) was refluxed for 2 hours under stirring and evaporated to dryness. The residue was triturated with diethyl ether to giver 1-[1-(aminomethyl)ethyl]-1H-tetrazole-5-thiol hydrochloride (19 g), mp 208° to 210° C.

I.R. (Nujol): 2800–2400, 1610, 1600, 1510, 1285, 1200, 1050 cm$^{-1}$.

N.M.R. (D$_2$O,δ): 1.62 (3H, d, J=7 Hz), 3.70 (2H, m), 5.23 (1H, m).

(4) To a solution of 1-[1-(aminomethyl)ethyl]-1H-tetrazole-5-thiol hydrochloride (17 g) and triethylamine (19.33 g) in 50% aqueous dioxane (80 ml) was added a solution of 2-t-butoxycarbonyloxyimino-2-phenylacetonitrile (21.4 g) in dioxane (50 ml) under cooling in an ice bath. The mixture was stirred for 1.5 hours at ambient temperature and concentrated to third volume. The aqueous solution was washed with diethyl ether and the washings were reextracted with aqueous solution of potassium carbonate. The two aqueous solutions were combined, washed with diethyl ether and mixed with ethyl acetate. The mixture was acidified with 10% hydrochloric acid and the organic layer was separated out. The solution was dried over magnesium sulfate and evaporated to dryness. The residue was triturated with n-hexane to give 1-[1-{(N-t-butoxycarbonylamino)methyl}ethyl]-1H-tetrazole-5-thiol (19.15 g), mp 156° to 158° C.

I.R. (Nujol): 3270, 3070, 2850, 1660, 1530, 1500, 1390, 1340, 1300, 1180, 1040 cm$^{-1}$.

N.M.R. (d$_6$-DMSO, δ): 1.40 (9H, s), 1.52 (3H, d, J=7 Hz), 3.41 (2H, m), 4.95 (1H, m), 7.05 (1H, m).

EXAMPLE 1

Preparation of 7-[2-Methoxyimino-2-(5-formamido-1,2,4-thiadiazol-3-yl)acetamido]-3-(1-methyl-1H-tetrazol-5-ylthiomethyl)-3-cephem-4-carboxylic acid (syn isomer).

A mixture of N,N-dimethylformamide (6 ml) and phosphorus oxychloride (918 mg) was stirred for 30 minutes at ambient temperature. To the mixture were added methylene chloride (6 ml) and 2-methoxyimino-2-(5-formamido-1,2,4-thiadiazol-3-yl)acetic acid (syn isomer) (1.1 g) at $-15°$ to $-10°$ C., followed by stirring for 30 minutes at the same temperature. A mixture of 7-amino-3-(1-methyl-1H-tetrazol-5-ylthiomethyl)-3-cephem-4-carboxylic acid (1.97 g) and trimethylsilylacetamide (6 g) in methylene chloride (60 ml) was warmed to make a clear solution. The solution was cooled to $-15°$ C. and added to the above obtained solution. The reaction mixture was stirred for an hour at 0° C. and poured into a cold aqueous solution of sodium bicarbonate. The aqueous layer was separated, adjusted to pH 2 with 10% hydrochloric acid and extracted with ethyl acetate. The extract was dried over anhydrous magnesium sulfate and evaporated to dryness. The residue was triturated with diethyl ether to give a crude product of the title compound (2.75 g). The crude material was dissolved in an aqueous solution of sodium bicarbonate and reprecipitated with diluted hydrochloric acid to give the pure title compound (1.5 g), mp. 170° to 175° C. (dec.).

I.R. (Nujol): 3300, 1780, 1680 cm$^{-1}$.

N.M.R. (d$_6$-DMSO, δ): 3.90 (2H, broad s), 3.95 L (3H, s), 4.00 (3H, s), 4.33 (2H, broad s), 5.17 (1H, d, J=4 Hz), 5.87 (1H, 2d, J=4, 8 Hz), 8.83 (1H, s), 9.70 (1H, d, J=8 Hz).

EXAMPLE 2

Preparation of 7-[2-Methoxyimino-2-(5-amino-1,2,4-thiadiazol-3-yl)acetamido]-3-(1-methyl-1H-tetrazol-5-ylthiomethyl)-3-cephem-4-carboxylic acid (syn isomer).

A mixture of 2-methoxyimino-2-(5-amino-1,2,4-thiadiazol-3-yl)acetic acid (syn isomer) (100 mg) and phosphorus oxychloride (306 mg) in methylene chloride (5 ml) was stirred for 30 minutes at ambient temperature. To the mixture was added N,N-dimethylformamide (0.2 ml) under cooling in an ice-bath, followed by stirring for 30 minutes. A mixture of 7-amino-3-(1-methyl-1H-tetrazol-5-ylthiomethyl)-3-cephem-4-carboxylic acid (300 mg) and trimethylsilylacetamide (0.9 g) in methylene chloride (9 ml) was warmed to make a clear solution. The solution was cooled in an ice-bath and added to the above obtained solution, followed by stirring for 30 minutes at 0° C. The reaction mixture was poured into a cold aqueous solution of sodium bicarbonate. The aqueous layer was separated, adjusted to pH 1 with 10% hydrochloric acid and extracted with ethyl acetate. The extract was dried over anhydrous magnesium sulfate and evaporated to dryness. The residue was triturated with diethyl ether to give a crude product of the title compound (120 mg). The crude material was dissolved in an aqueous solution of sodium bicarbonate and reprecipitated with diluted hydrochloric acid to give the pure title compound (60 mg), mp. 170° to 175° C. (dec.).

I.R. (Nujol): 3300, 1770, 1660, 1610, 1520 cm$^{-1}$.

N.M.R. (d$_6$-DMSO, δ): 3.73 (2H, broad s), 3.97 (6H, s), 4.33 (2H, broad s), 5.13 (1H, d, J=4 Hz), 5.83 (1H, 2d, J=4, 8.5 Hz), 8.12 (2H, s), 9.57 (1H, d, J=8.5 Hz).

EXAMPLE 3

Preparation of 7-[2-Methoxyimino-2-(5-amino-1,2,4-thiadiazol-3-yl)acetamido]cephalosporanic acid (syn isomer).

A mixture of 2-methoxyimino-2-(5-amino-1,2,4-thiadiazol-3-yl)acetic acid (syn isomer) (1.21 g) and phosphorus oxychloride (3.67 g) in methylene chloride (30 ml) was stirred for an hour at ambient temperature, cooled and thereto was added N,N-dimethylformamide (2.4 ml), followed by stirring for an additional 30 minutes under ice-cooling. A mixture of 7-aminocephalosporanic acid (2.94 g) and trimethylsilylacetamide (10 g) in methylene chloride (50 ml) was warmed to make a clear solution. The solution was cooled in an ice-bath and added to the above obtained solution, followed by stirring for 30 minutes at 0° to 5° C. The reaction mixture was poured into a mixture of a saturated aqueous solution of sodium bicarbonate (60 ml) and ice. The aqueous layer (200 ml., pH 7 to 8) was separated and thereto was added ethyl acetate. The resulting mixture was adjusted to pH 1 with 10% hydrochloric acid, saturated with sodium chloride and filtered to remove an insoluble material. The ethyl acetate layer was separated, dried over magnesium sulfate and evaporated. The residue was triturated with diethyl ether to give a crude product of the title compound (2.4 g). The crude material was dissolved in an aqueous solution of sodium bicarbonate, treated with activated charcoal (100 mg), adjusted to pH 2 with 10% hydrochloric acid. The precipitates were collected by filtration, washed with ice-water and dried to give the title compound (1.2 g), mp. 180° to 185° C. (dec.).

I.R. (Nujol): 3350, 1780, 1730, 1680, 1620, 1530 cm$^{-1}$.

N.M.R. (d$_6$-DMSO, δ): 1.97 (3H, s), 3.50 (2H, s), 3.87 (3H, s), $\left\{ \begin{array}{l} 4.67 \\ 4.93 \end{array} \right.$ (2H, ABq, J = 14Hz), 5.08 (1H, d, J=4 Hz), 5.77 (1H, 2d, J=4, 8.5 Hz), 8.06 (2H, s), 9.50 (1H, d, J=8.5 Hz).

EXAMPLE 4

Preparation of 7-[2-Methoxyimino-2-(5-amino-1,2,4-thiadiazol-3-yl)acetamido]-3-carbamoyloxymethyl-3-cephem-4-carboxylic acid (syn isomer).

A mixture of 2-methoxyimino-2-(5-amino-1,2,4-thiadiazol-3-yl)acetic acid (syn isomer) (1.01 g) and phosphorus oxychloride (3.06 g) in methylene chloride (25 ml) was stirred for 2 hours at ambient temperature, cooled to 0° C. and thereto was added N,N-dimethylformamide (2.0 ml), followed by stirring for an additional 45 minutes at 0° C. A mixture of 7-amino-3-carbamoyloxymethyl-3-cephem-4-carboxylic acid (4.9 g) and trimethylsilylacetamide (11 g) in methylene chloride (100 ml) was warmed to make a clear solution. The solution was cooled to −15° C. and added to the above obtained solution, followed by stirring for 30 minutes at 0° C. The reaction mixture was poured into a cold aqueous solution of sodium bicarbonate. The aqueous layer was separated and thereto was added ethyl acetate. The resulting mixture was adjusted to pH 2 with 10% hydrochloric acid, filtered to remove an insoluble material and then saturated with sodium chloride. The ethyl acetate layer was separated, dried over magnesium sulfate and evaporated. The residue was triturated with diethyl ether to give a crude product of the title compound (1.2 g). The crude material was dissolved in an aqueous solution of sodium bicarbonate, and reprecipitated with 10% hydrochloric acid. The precipitates were collected by filtration, washed with water and dried to give the title compound (0.35 g), mp. 185° to 190° C. (dec.).

I.R. (Nujol): 3350, 1780, 1720, 1680, 1620, 1530 cm$^{-1}$.

N.M.R. (d$_6$-DMSO, δ): 3.52 (2H, s), 3.92 (3H, s), $\left\{ \begin{array}{l} 4.62 \\ 4.88 \end{array} \right.$ (2H, ABq, J = 12Hz)

5.14 (1H, d, J=4 Hz), 5.80 (1H, 2d, J=4,8 Hz), 6.58 (2H, s), 8.10 (2H, s), 9.54 (1H, d, J=8 Hz).

EXAMPLE 5

Preparation of 7-[2-Methoxyimino-2-(5-amino-1,2,4-thiadiazol-3-yl)acetamido]-2-methyl-3-cephem-4-carboxylic acid (syn isomer).

A mixture of 2-methoxyimino-2-(5-amino-1,2,4-thiadiazol-3-yl)acetic acid (syn isomer) (1.21 g) and phosphorus oxychloride (3.67 g) in methylene chloride (30 ml) was stirred for two hours at ambient temperature, cooled to 0° C. and thereto was added N,N-dimethylformamide (2.4 ml), followed by stirring for an additional 45 minutes at 0° C. A mixture of 7-amino-2-methyl-3-cephem-4-carboxylic acid (3.0 g) and trimethylsilylacetamide (10 g) in methylene chloride (50 ml) was warmed to make a clear solution. The solution was cooled to −15° C. and added to the above obtained solution, followed by stirring for 30 minutes at 0° C. The reaction mixture was poured into a cold aqueous solution of sodium bicarbonate. The aqueous layer was separated and thereto was added ethyl acetate. The resulting mixture was adjusted to pH 2 with 10% hydrochloric acid and the ethyl acetate layer was separated, dried over anhydrous magnesium sulfate and then evaporated. The residue was triturated with diethyl ether to give a crude product of the title compound (2.2 g). The crude material was dissolved in an aqueous solution of sodium bicarbonate, adjusted to pH 2 with 10% hydrochloric acid. The precipitates were collected by filtration, washed with ice-water and dried to give the title compound (1.6 g), mp. 175° to 180° C. (dec.).

I.R. (Nujol): 3350, 1775, 1675, 1630, 1530 cm$^{-1}$.

N.M.R. (d$_6$-DMSO, δ): 1.43 (3H, d, J=6 Hz), 3.6–3.9 (1H, m), 3.93 (3H, s), 5.07 (1H, d, J=4 Hz), 5.87 (1H, 2d, J=4,8 Hz), 6.53 (1H, d, J=5 Hz), 8.08 (2H, s), 9.55 (1H, d, J=8 Hz).

EXAMPLE 6

Preparation of 4-Nitrobenzyl 7-[2-methoxyimino-2-(5-amino-1,2,4-thiadiazol-3-yl)acetamido]-3-cephem-4-carboxylate (syn isomer) (I) and 4-nitrobenzyl 7-[2-methoxyimino-2-{5-{N'-(N,N-dimethylaminomethylene)amino}-1,2,4-thiadiazol-3-yl}acetamido]-3-cephem-4-carboxylate (syn isomer) (II).

A mixture of 2-methoxyimino-2-(5-amino-1,2,4-thiadiazol-3-yl)acetic acid (syn isomer) (1.21 g) and phosphorus oxychloride (3.67 g) in methylene chloride (30 ml) was stirred for 2 hours at ambient temperature, cooled to 0° C. and thereto was added N,N-dimethylformamide (2.4 ml), followed by stirring for an additional 45 minutes at 0° C. A mixture of 4-nitrobenzyl 7-amino-3-cephem-4-carboxylate (2.68 g) and trimethylsilylacetamide (8 g) in methylene chloride (80 ml) was stirred for 2 hours at ambient temperature to make a clear solution. The solution was cooled to 0° C. and added to the above obtained solution, followed by stirring for 30 minutes at 0° to 5° C. The reaction mixture was poured into a cold aqueous solution of sodium bicarbonate. The methylene chloride layer was separated, dried over magnesium sulfate and evaporated. The residue was triturated with diethyl ether to give a mixture of crude product of the title compound (I) and (II) (3.7 g). The crude powder was subjected to column chromatography on silica gel using ethyl acetate as an eluent to firstly give the title compound (I) (1.0 g), mp. 150° to 155° C. From subsequent fractions, there was obtained the title compound (II) (1.1 g), mp. 115° to 120° C. The title compound (I) has the following I.R. and N.M.R. spectra;

I.R. (Nujol): 3300, 1770, 1720, 1670, 1620, 1510 cm$^{-1}$.

N.M.R. (d$_6$-DMSO, δ): 3.63 (2H, broad d, J=3 Hz), 3.93 (3H, s), 5.17 (1H, d, J=4 Hz), 5.43 (2H, s), 5.92 (1H, 2d, J=4,9 Hz), 6.67 (1H, t, J=3 Hz), 7.70 (2H, d, J=8 Hz), 8.08 (2H, s), 8.23 (2H, d, J=8 Hz), 9.55 (1H, d, J=9 Hz).

The title compound (II) has the following I.R. and N.M.R. spectra;

I.R. (Nujol): 3300, 1770, 1720, 1670, 1610 cm$^{-1}$.

N.M.R. (d$_6$-DMSO, δ): 3.07 (3H, s), 3.20 (3H, s), 3.63 (2H, broad d, J=3 Hz), 3.97 (3H, s), 5.17 (1H, d, J=4 Hz), 5.43 (2H, s), 5.93 (1H, 2d, J=4,8 Hz), 6.67 (1H, t, J=3 Hz), 7.70 (2H, d, J=8 Hz), 8.23 (2H, d, J=8 Hz), 8.47 (1H, s), 9.60 (1H, d, J=8 Hz).

EXAMPLE 7

A mixture of 2-ethoxyimino-2-(5-amino-1,2,4-thiadiazol-3-yl)acetic acid (syn isomer) (1.3 g) and phosphorus oxychloride (3.67 g) in methylene chloride (30 ml) was stirred for 2 hours at ambient temperature and then cooled to −12° to −15° C. To the cold mixture was added dimethylformamide (2.4 ml) and the mixture was stirred for 45 minutes at −8° to −10° C. On the other hand, a mixture of 7-amino-3-(1,3,4-thiadiazol-2-yl)thiomethyl-3-cephem-4-carboxylic acid (2.9 g) and trimethylsilylacetamide (8 g) in methylene chloride (40 ml) was warmed to make a solution. The solution was cooled to −25° C. and added to the above activated mixture. The reaction mixture was stirred for 30 minutes at −8° to −10° C. and poured into a cold aqueous solution of sodium bicarbonate. The mixture was stirred for 30 minutes at ambient temperature and the aqueous layer was separated out. The aqueous solution was adjusted to pH 1 with 10% hydrochloric acid and extracted with ethyl acetate. The extract was dried over magnesium sulfate and evaporated to dryness. The residue was triturated with diethyl ether to give a crude 7-[2-ethoxyimino-2-(5-amino-1,2,4-thiadiazol-3-yl)acetamido]-3-(1,3,4-thiadiazol-2-yl)thiomethyl-3-cephem-4-carboxylic acid (syn isomer) (2.6 g). The crude product was dissolved in an aqueous solution of sodium bicarbonate and reprecipitated with an addition of 10% hydrochloric acid to give pure object compound (1.92 g). mp 150° to 155° C. (dec.)

I.R. (Nujol): 3350, 3230, 1775, 1680, 1620, 1530 cm$^{-1}$.

N.M.R. (d$_6$-DMSO, δ): 1.27 (3H, t, J=7 Hz), 3.72 (2H, broad s), 4.22 (2H, q, J=7 Hz) 4.32 and 4.55 (2H, ABq, J=13 Hz), 5.17 (1H,d, J=5 Hz), 5.83 (1H, dd, J=5 and 8 Hz), 8.13 (2H, broad s), 9.56 (1H, d, J=8 Hz), 9.57 (1H, s).

EXAMPLE 8

A mixture of 2-isopropoxyimino-2-(5-amino-1,2,4-thiadiazol-3-yl)acetic acid (syn isomer) (1.38 g) and phosphorus oxychloride (3.67 g) in methylene chloride (30 ml) was stirred for 1.5 hours at ambient temperature and then cooled to −12° to −15° C. To the cold mixture was added dimethylformamide (2.4 ml) and the mixture was stirred for 45 minutes at −8° to −10° C. On the other hand, a mixture of 7-amino-3-(1,3,4-thiadiazol-2-yl)thiomethyl-3-cephem-4-carboxylic acid (2.9 g) and trimethylsilylacetamide (8 g) in methylene chloride (40 ml) was warmed to make a solution. The solution was cooled to −25° C. and added to the above activated mixture. The reaction mixture was stirred for 30 minutes at −10° C. and poured into a cold aqueous solution of sodium bicarbonate. The mixture was stirred for 30 minutes at ambient temperature and the aqueous layer was separated out. The aqueous solution was adjusted to pH 1 with 10% hydrochloric acid and extracted with ethyl acetate. The extract was dried over magnesium sulfate and evaporated to dryness. The residue was triturated with diethyl ether to give a crude 7-[2-isopropoxyimino-2-(5-amino-1,2,4-thiadiazol-3-yl)acetamido]-3-(1,3,4-thiadiazol-2-yl)thiomethyl-3-cephem-4-carboxylic acid (syn isomer) (2.25 g). The crude product was dissolved in a mixture of acetone and ethyl acetate. The acetone was evaporated and the precipitates were collected by filtration to give the same object compound (1.53 g), which was dissolved in an aqueous solution of sodium bicarbonate and reprecipitated with an addition of 10% hydrochloric acid to give pure object compound (1.23 g). mp 145° to 150° C. (dec.)

I.R. (Nujol): 3370, 3230, 1780, 1680, 1625, 1530 cm$^{-1}$.

N.M.R. (d$_6$-DMSO, δ): 1.25 (6H, d, J=6 Hz), 3.68 (2H, broad s), 4.2–4.6 (1H, m), 4.28 and 4.55 (2H, ABq, J=13 Hz), 5.13 (1H, d, J=5 Hz), 5.80 (1H, dd, J=5 and 8 Hz) 8.12 (2H, broad s), 9.50 (1H, d, J=8 Hz), 9.53 (1H, s).

EXAMPLE 9

A mixture of phosphorus pentachloride (250 mg) and methylene chloride (5 ml) was stirred for 10 minutes at ambient temperature. 2-Isopropoxyimino-2-(5-amino-1,2,4-thiadiazol-3-yl)acetic acid (syn isomer) (230 mg) was added thereto at −15° C. and the mixture was stirred for 45 minutes at −10° to −13° C. A solution of 7-aminocephalosporanic acid (350 mg) and trimethylsilylacetamide (1 g) in methylene chloride (5 ml) was added thereto at −15° C. and the mixture was stirred for 30 minutes at −10° C. To the reaction mixture were added a saturated aqueous solution of sodium bicarbonate (8 ml) and water (10 ml), and then methylene chloride was evaporated. To the aqueous layer was added ethyl acetate, and the mixture was adjusted to pH 2 with 10% hydrochloric acid and then extracted with ethyl acetate. The extract was dried over magnesium sulfate and concentrated. The residue was triturated with diethyl ether and precipitates were collected by filtration to give 7-[2-isopropoxyimino-2-(5-amino-1,2,4-thiadiazol-3-yl)acetamido]cephalosporanic acid (syn isomer) (450 mg). mp 150° to 155° C. (dec.)

I.R. (Nujol): 3300, 1780, 1725, 1660, 1520 cm$^{-1}$.

N.M.R. (d$_6$-DMSO, δ): 1.30 (6H, d, J=6 Hz), 2.08 (3H, s), 3.62 (2H, broad s), 4.33–4.67 (1H, m), 4.77 and 5.03 (2H, ABq, J=13 Hz), 5.22 (1H, d, J=4 Hz), 5.87 (1H, dd, J=4 and 8 Hz), 8.17 (2H, s), 9.53 (1H, d, J=8 Hz).

EXAMPLE 10

To a cold solution of phosphorus pentachloride (2.5 g) in methylene chloride (60 ml) was added 2-ethoxyimino-2-(5-amino-1,2,4-thiadiazol-3-yl)acetic acid (syn isomer) (2.16 g) at −15° C. and the mixture was stirred for 30 minutes at the same temperature. On the other hand, a mixture of 4-nitrobenzyl 7-amino-3-cephem-4-carboxylate (4.0 g) and trimethylsilylacetamide (12 g) in methylene chloride (60 ml) was warmed to make a clear solution and then cooled to −10° C. The solution was added to the above activated mixture and the mixture was stirred for 0.5 hour at 0° to 5° C. The reaction mixture was poured into cold aqueous solution (150 ml) of sodium bicarbonate (7.0 g). The organic layer was dried over magnesium sulfate and evaporated to dryness. The residue was pulverized with diethyl ether and precipitates were collected by filtration and dried to give 4-nitrobenzyl 7-[2-ethoxyimino-2-(5-amino-1,2,4-thiadiazol-3-yl)acetamido]-3-cephem-4-carboxylate (syn isomer) (5.5 g), mp. 120° to 125° C. (dec.).

I.R. (Nujol): 3300, 1770, 1720, 1670, 1620, 1605, 1520 cm$^{-1}$.

N.M.R. (d$_6$-DMSO, δ): 1.23 (3H, t, J=7 Hz), 3.50–3.70 (2H, m), 4.33 (2H, q, J=7 Hz), 5.10 (1H, d, J=4 Hz), 5.37 (2H, s), 5.88 (1H, dd, J=4 and 8 Hz), 6.60 (1H, t, J=4 Hz), 7.63 (2H, d, J=8 Hz), 8.07 (2H, s), 8.17 (2H, d, J=8 Hz), 9.50 (1H, d, J=8 Hz).

EXAMPLE 11

The following compounds were prepared by similar manners to those described in Examples 1 to 10.

(1) 7-[2-Methoxyimino-2-(5-amino-1,2,4-thiadiazol-3-yl)acetamido]-3-(5-methyl-1,3,4-thiadiazol-2-ylthiomethyl)-3-cephem-4-carboxylic acid (syn isomer), mp. 175° to 180° C. (dec.).

I.R. (Nujol): 3350, 1780, 1680, 1625, 1530 cm$^{-1}$.

N.M.R. (d$_6$-DMSO, δ): 2.72 (3H, s), 3.70 (2H, s), 4.00 (3H, s), 4.25, 4.53 (2H, ABq, J=14 Hz), 5.16 (1H, d, J=4 Hz), 5.83 (1H, 2d, J=4,8 Hz), 8.13 (2H, s), 9.58 (1H, d, J=8 Hz).

(2) 7-[2-Methoxyimino-2-(5-amino-1,2,4-thiadiazol-3-yl)acetamido]-3-(1,3,5-thiadiazol-2-ylthiomethyl)-3-cephem-4-carboxylic acid (syn isomer), mp. 172° to 177° C. (dec.).

I.R. (Nujol): 3350, 1775, 1680, 1625, 1530 cm$^{-1}$.

N.M.R. (d$_6$-DMSO, δ): 3.80 (2H, s), 4.00 (3H, s), 4.38, 4.67 (2H, ABq, J=14 Hz), 5.22 (1H, d, J=5 Hz), 5.90 (1H, 2d, J=5,8 Hz), 8.20 (2H, s), 9.63 (1H, s), 9.67 (1H, d, J=8 Hz).

(3) 7-[2-Methoxyimino-2-(5-amino-1,2,4-thiadiazol-3-yl)acetamido]-3-(1-allyl-1H-tetrazol-5-ylthiomethyl)-3-cephem-4-carboxylic acid (syn isomer), mp. 170° to 172° C. (dec.).

I.R. (Nujol): 3350, 1780, 1680, 1625, 1530 cm$^{-1}$.

N.M.R. (d$_6$-DMSO, δ): 3.67 (2H, s), 3.93 (3H, s), $\left\{\begin{array}{l} 4.23 \\ 4.43 \end{array}\right.$ (2H, ABq, J = 13Hz), 4.9–5.5 (5H, m), 5.6–6.3 (2H, m), 8.10 (2H, s), 9.53 (1H, d, J=8 Hz).

(4) 7-[2-Methoxyimino-2-(5-amino-1,2,4-thiadiazol-3-yl)acetamido]-3-cephem-4-carboxylic acid (syn isomer), mp. 190° to 195° C. (dec.).

I.R. (Nujol): 3350, 1775, 1680, 1630, 1530 cm$^{-1}$.

(5) 7-[2-Propoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 133° C. (dec.)

I.R. (Nujol): 3380, 3230, 1780, 1680, 1625, 1530 cm$^{-1}$.

N.M.R. (d$_6$-DMSO, δ): 0.92 (3H, t, J=6 Hz), 1.3–2.1 (2H, m), 3.12 (2H, t, J=6 Hz), 3.72 (2H, broad s), 4.33 and 4.58 (2H, ABq, J=13 Hz), 5.17 (1H, d, J=5 Hz), 5.82 (1H, dd, J=5 and 8 Hz), 8.12 (2H, broad s), 9.53 (1H, d, J=8 Hz), 9.57 (1H, s).

(6) 7-[2-Methoxyimino-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp 150° to 155° C. (dec.)

I.R. (Nujol): 3350, 3250, 1780, 1670 cm$^{-1}$.

N.M.R. (d$_6$-DMSO, δ): 1.40 (9H, s), 3.70 (2H, broad s), 3.93 (3H, s), 4.30 and 4.53 (2H, ABq, J=13 Hz), 4.53

(2H, d, J=5 Hz), 5.17 (1H, d, J=4 Hz), 5.83 (1H, dd, J=4 and 8 Hz), 8.13 (2H, s), 9.57 (1H, d, J=8 Hz).

(7) 7-[2-Methoxyimino-2-(5-amino-1,2,4-thiadiazol-3-yl)acetamido]-3-(5-allylthio-1,3,4-thiadiazol-2-yl)thiomethyl-3-cephem-4-carboxylic acid (syn isomer). mp 160° to 165° C. (dec.)

I.R. (Nujol): 3350, 3250, 1780, 1680, 1620 cm$^{-1}$.

N.M.R. (d$_6$-DMSO, δ): 3.70 (2H, broad s), 3.9–4.0 (2H, m), 3.93 (3H, s), 4.27 and 4.50 (2H, ABq, J=14 Hz), 5.15 (1H, d, J=4 Hz), 5.1–5.5 (2H, m), 5.6–6.2 (1H, m), 5.83 (1H, dd, J=4 and 8 Hz), 8.13 (2H, s), 9.57 (1H, d, J=8 Hz).

(8) 7-[2-Methoxyimino-2-(5-amino-1,2,4-thiadiazol-3-yl)acetamido]-3-acetylthiomethyl-3-cephem-4-carboxylic acid (syn isomer). mp 178° to 182° C. (dec.)

I.R. (Nujol): 3350, 3250, 1780, 1680, 1620 cm$^{-1}$.

N.M.R. (d$_6$-DMSO, δ): 2.83 (3H, s), 3.27 and 3.57 (2H, ABq, J=18 Hz), 3.83 (3H, s), 3.73 and 3.97 (2H, ABq, J=13 Hz), 5.04 (1H, d, J=4 Hz), 5.72 (1H, d, J=4 Hz), 5.72 (1H, dd, J=4 and 8 Hz), 8.07 (2H, s), 9.47 (1H, d, J=8 Hz).

(9) 7-[2-Methoxyimino-2-(5-amino-1,2,4-thiadiazol-3-yl)acetamido]-3-pyrazinylthiomethyl-3-cephem-4-carboxylic acid (syn isomer). mp 170° to 174° C. (dec.)

I.R. (Nujol): 3350, 3250, 1780, 1680, 1620, 1530 cm$^{-1}$.

(10) 7-[2-Methoxyimino-2-(5-amino-1,2,4-thiadiazol-3-yl)acetamido]-3-(2-thiazolin-2-yl)thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

(11) 7-[2-Methoxymino-2-(5-amino-1,2,4-thiadiazol-3-yl)acetamido]-3-(tetrazolo[1,5-b]pyridazin-6-yl)thiomethyl-3-cephem-4-carboxylic acid (syn isomer). mp 175° to 180° C. (dec.)

I.R. (Nujol): 3400, 3250, 1885, 1725, 1670, 1640, 1540 cm$^{-1}$.

(12) 7-[2-Methoxyimino-2-(5-amino-1,2,4-thiadiazol-3-yl)acetamido]-3-[1-{2-(N-t-butoxycarbonylamino)-ethyl}-1H-tetrazol-5-yl]thiomethyl-3-cephem-4-carboxylic acid (syn isomer). mp 200° to 205° C. (dec.)

I.R. (Nujol): 3300, 1780, 1700, 1680, 1620, 1520 cm$^{-1}$.

(13) 7-[2-Methoxyimino-2-(5-amino-1,2,4-thiadiazol-3-yl)acetamido]-3-(1-propyl-1H-tetrazol-5-yl)thiomethyl-3-cephem-4-carboxylic acid (syn isomer). mp 155° to 160° C. (dec.)

I.R. (Nujol): 3350, 3250, 1780, 1680, 1630, 1530 cm$^{-1}$.

(14) 7-[2-Methoxyimino-2-(5-amino-1,2,4-thiadiazol-3-yl)acetamido]-3-[1-(3-methoxypropyl)-1H-tetrazol-5-yl]thiomethyl-3-cephem-4-carboxylic acid (syn isomer). mp 165° to 167° C. (dec.)

I.R. (Nujol): 3350, 3250, 1780, 1680, 1620, 1530 cm$^{-1}$.

(15) 7-[2-Methoxyimino-2-(5-amino-1,2,4-thiadiazol-3-yl)acetamido]-3-(3-methyl-1,2,4-thiadiazol-5-yl)thiomethyl-3-cephem-4-carboxylic acid (syn isomer). mp 178° to 182° C. (dec.)

I.R. (Nujol): 3350, 3250, 1780, 1680, 1630, 1530 cm$^{-1}$.

(16) 7-[2-Methoxyimino-2-(5-amino-1,2,4-thiadiazol-3-yl)acetamido]-3-(5-methoxymethyl-1,3,4-thiadiazol-2-yl)thiomethyl-3-cephem-4-carboxylic acid (syn isomer). mp 170° to 174° C. (dec.)

I.R. (Nujol): 3350, 3250, 1780, 1680, 1630, 1530 cm$^{-1}$.

(17) 7-[2-Methoxyimino-2-(5-amino-1,2,4-thiadiazol-3-yl)acetamido]-3-(5-methylthiomethyl-1,3,4-thiadiazol-2-yl)thiomethyl-3-cephem-4-carboxylic acid (syn isomer). mp 173° to 175° C. (dec.)

I.R. (Nujol): 3350, 3250, 1780, 1680, 1630, 1530 cm$^{-1}$.

(18) 7-[2-Methoxyimino-2-(5-amino-1,2,4-thiadiazol-3-yl)acetamido]-3-(4-propyl-4H-1,2,4-triazol-3-yl)thiomethyl-3-cephem-4-carboxylic acid (syn isomer). mp 182° to 184° C. (dec.)

I.R. (Nujol): 3350, 3250, 1780, 1680, 1620, 1530 cm$^{-1}$.

(19) 7-[2-Methoxyimino-2-(5-amino-1,2,4-thiadiazol-3-yl)acetamido]-3-(1-methylthiomethyl-1H-tetrazol-5-yl)thiomethyl-3-cephem-4-carboxylic acid (syn isomer). mp 175° to 178° C. (dec.)

I.R. (Nujol): 3350, 3250, 1780, 1680, 1620, 1530 cm$^{-1}$.

(20) 7-[2-Methoxyimino-2-(5-amino-1,2,4-thiadiazol-3-yl)acetamido]-3-(1-isopropyl-1H-tetrazol-5-yl)thiomethyl-3-cephem-4-carboxylic acid (syn isomer). mp 180° to 182° C. (dec.)

I.R. (Nujol): 3350, 3250, 1780, 1680, 1630, 1530 cm$^{-1}$.

(21) 7-[2-Methoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer). mp 170° to 175° C. (dec.)

I.R. (Nujol): 3350, 3250, 1780, 1680, 1625, 1530 cm$^{-1}$.

(22) 7-[2-Methoxyimino-2-(5-amino-1,2,4-thiadiazol-3-yl)acetamido]-3-[5-(2-hydroxyethyl)-1,3,4-thiadiazol-2-yl]thiomethyl-3-cephem-4-carboxylic acid (syn isomer). mp 175° to 180° C. (dec.)

I.R. (Nujol): 3350, 3250, 1780, 1680, 1630, 1530 cm$^{-1}$.

(23) 7-[2-Methoxyimino-2-(5-amino-1,2,4-thiadiazol-3-yl)acetamido]-3-(5-propyl-1,3,4-thiadiazol-2-yl)thiomethyl-3-cephem-4-carboxylic acid (syn isomer). mp 177° to 180° C. (dec.)

I.R. (Nujol): 3350, 3250, 1780, 1680, 1630, 1530 cm$^{-1}$.

(24) 7-[2-Methoxyimino-2-(5-amino-1,2,4-thiadiazol-3-yl)acetamido]-3-(5-hydroxymethyl-1,3,4-thiadiazol-2-yl)thiomethyl-3-cephem-4-carboxylic acid (syn isomer). mp 165° to 170° C. (dec.)

I.R. (Nujol): 3350, 3250, 1780, 1680, 1620, 1530 cm$^{-1}$.

(25) 7-[2-Methoxyimino-2-(5-amino-1,2,4-thiadiazol-3-yl)acetamido]-3-(5-methanesulfonamidomethyl-1,3,4-thiadiazol-2-yl)thiomethyl-3-cephem-4-carboxylic acid (syn isomer). mp 170° to 175° C. (dec.)

I.R. (Nujol): 3350, 3250, 1780, 1680, 1620, 1530 cm$^{-1}$.

(26) 7-[2-Methoxyimino-2-(5-amino-1,2,4-thiadiazol-3-yl)acetamido]-3-(3-allylthio-1,2,4-thiadiazol-5-yl)thiomethyl-3-cephem-4-carboxylic acid (syn isomer). mp 170° to 173° C. (dec.)

I.R. (Nujol): 3350, 3250, 1780, 1680, 1620, 1530 cm$^{-1}$.

(27) 7-[2-Methoxyimino-2-(5-amino-1,2,4-thiadiazol-3-yl)acetamido]-3-(5-mesylmethyl-1,3,4-thiadiazol-2-yl)thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

(28) Sodium 7-[2-methoxyimino-2-(5-amino-1,2,4-thiadiazol-3-yl)acetamido]-3-(1-sulfonatomethyl-1H-tetrazol-5-yl)thiomethyl-3-cephem-4-carboxylic acid (syn isomer). mp 205° to 210° C. (dec.)

I.R. (Nujol): 3350, 3250, 1780, 1680, 1530 cm$^{-1}$.

(29) 7-[2-Methoxyimino-2-(5-amino-1,2,4-thiadiazol-3-yl)acetamido]-3-(4-methyl-4H-1,2,4-triazol-3-yl)thiomethyl-3-cephem-4-carboxylic acid (syn isomer). mp 180° to 185° C. (dec.)

I.R. (Nujol): 3350, 3250, 1780, 1680, 1620, 1530 cm$^{-1}$.

(30) 7-[2-Methoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer). mp 185° to 190° C. (dec.)

I.R. (Nujol): 3350, 3250, 1780, 1680, 1620, 1530 cm$^{-1}$.

(31) 7-[2-Methoxyimino-2-(5-amino-1,2,4-thiadiazol-3-yl)acetamido]-3-[4-(3-methoxypropyl)-4H-1,2,4-triazol-3-yl]thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

(32) 7-[2-Methoxyimino-2-(5-amino-1,2,4-thiadiazol-3-yl)acetamido]-3-[5-(2-aminoethyl)-1,3,4-thiadiazol-2-yl]thiomethyl-3-cephem-4-carboxylic acid (syn isomer). mp 205° to 210° C. (dec.)

I.R. (Nujol): 3200, 1770, 1670, 1620, 1530 cm$^{-1}$.

(33) 7-[2-Methoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 210° to 215° C. (dec.)

I.R. (Nujol): 3350, 3200, 1770, 1680, 1620 cm$^{-1}$.

(34) 7-[2-Methoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 200° to 205° C. (dec.)

I.R. (Nujol): 3350, 3200, 1775, 1670, 1620, 1530 cm$^{-1}$.

(35) 7-[2-Ethoxyimino-2-(5-amino-1,2,4-thiadiazol-3-yl)acetamido]cephalosporanic acid (syn isomer). mp 140° to 156° C. (dec.)

I.R. (Nujol): 3370, 3250, 1780, 1730, 1680, 1620, 1530, 1380, 1240, 1040 cm$^{-1}$.

N.M.R. (d$_6$-DMSO, δ): 1.23 (3H, t, J=7 Hz), 2.00 (3H, s), 3.7 (2H, m), 4.17 (2H, q, J=7 Hz), 4.63 and 5.00 (2H, ABq, J=12 Hz), 5.10 (1H, d, J=4.5 Hz), 5.80 (1H, dd, J=4.5 and 8.0 Hz), 8.1 (2H, broad s), 9.53 (1H, d, J=8 Hz).

(36) 7-[2-Ethoxyimino-2-(5-amino-1,2,4-thiadiazol-3-yl)acetamido]-3-[1-{3-(N-t-butoxycarbonylamino)-propyl}-1H-tetrazol-5-yl]thiomethyl-3-cephem-4-carboxylic acid (syn isomer). mp 183° to 188° C. (dec.)

I.R. (Nujol): 3370, 3240, 1780, 1690, 1630, 1530, 1380, 1260, 1170, 1040 cm$^{-1}$.

(37) 7-[2-Ethoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer).

I.R. (Nujol): 3360, 3240, 1780, 1690, 1630, 1530, 1375, 1250, 1170, 1040 cm$^{-1}$.

(38) 7-[2-Ethoxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 156° to 159° C. (dec.)

I.R. (Nujol): 3360, 3250, 1780, 1680, 1625, 1380, 1080, 1040 cm$^{-1}$.

(39) 7-[2-Ethoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer). mp 177° to 180° C. (dec.)

I.R. (Nujol): 3380, 3250, 1775, 1670, 1535, 1380, 1040 cm$^{-1}$.

(40) 7-[2-Ethoxyimino-2-(5-amino-1,2,4-thiadiazol-3-yl)acetamido]-3-(1-allyl-1H-tetrazol-5-yl)thiomethyl-3-cephem-4-carboxylic acid (syn isomer). mp 160° to 165° C. (dec.).

I.R. (Nujol): 3380, 3250, 1780, 1680, 1630, 1530, 1380, 1040 cm$^{-1}$.

(41) 7-[2-Ethoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 180° to 185° C. (dec.)

I.R. (Nujol): 3350, 3240, 1780, 1680, 1620, 1530, 1380, 1040 cm$^{-1}$.

(42) 7-[2-Ethoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 198° to 205° C. (dec.)

I.R. (Nujol): 3350, 3250, 1775, 1680, 1535, 1380, 1040 cm$^{-1}$.

(43) 7-[2-Ethoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer). mp 170° to 173° C. (dec.)

I.R. (Nujol): 3350, 3240, 1780, 1675, 1625, 1530, 1380, 1040, 720 cm$^{-1}$.

(44) 7-[2-Methoxyimino-2-(5-amino-1,2,4-thiadiazol-3-yl)acetamido]-3-(4-allyl-4H-1,2,4-triazol-3-yl)thiomethyl-3-cephem-4-carboxylic acid (syn isomer). mp 185° to 190° C. (dec.)

I.R. (Nujol): 3350, 3250, 1780, 1680, 1625, 1530 cm$^{-1}$.

(45) 7-[2-Methoxyimino-2-(5-amino-1,2,4-thiadiazol-3-yl)acetamido]-3-(3-methoxycarbonyl-1,2,4-thiadiazol-5-yl)thiomethyl-3-cephem-4-carboxylic acid (syn isomer). mp 180° to 185° C. (dec.)

I.R. (Nujol): 3350, 3250, 1780, 1740, 1680, 1620, 1530 cm$^{-1}$.

(46) 7-[2-Methoxyimino-2-(5-amino-1,2,4-thiadiazol-3-yl)acetamido]-3-(3-carboxy-1,2,4-thiadiazol-5-yl)thiomethyl-3-cephem-4-carboxylic acid (syn isomer). mp 175° to 180° C. (dec.)

I.R. (Nujol): 3350, 3250, 1780, 1730, 1680, 1620, 1530 cm$^{-1}$.

(47) 7-[2-Ethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer). mp 182° to 185° C. (dec.).

I.R. (Nujol): 3350, 3200, 1770, 1670, 1620, 1530, 1380, 1040 cm$^{-1}$.

(48) 7-[2-Ethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 195° to 210° C. (dec.).

I.R. (Nujol): 3340, 3210, 1770, 1675, 1620, 1530, 1380, 1040 cm$^{-1}$.

(49) 4-Nitrobenzyl 7-[2-isopropoxyimino-2-(5-amino-1,2,4-thiadiazol-3-yl)acetamido]-3-cephem-4-carboxylate (syn isomer), mp. 145° to 150° C. (dec.).

I.R. (Nujol): 3300, 1775, 1720, 1670, 1620, 1600, 1520 cm$^{-1}$.

N.M.R. (d$_6$-DMSO, δ): 1.27 (6H, d, J=7 Hz), 3.53–3.77 (2H, m), 4.17–4.67 (1H, m), 5.17 (1H, d, J=4 Hz), 5.42 (2H, s), 5.93 (1H, dd, J=4 and 8 Hz), 6.67 (1H, t, J=4 Hz), 7.86 (2H, d, J=8 Hz), 8.13 (2H, s), 8.23 (2H, d, J=8 Hz), 9.53 (1H, d, J=8 Hz).

(50) 7-[2-Isopropoxyimino-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp. 140° to 145° C. (dec.).

I.R. (Nujol): 3300, 1780, 1670, 1620, 1530 cm$^{-1}$.

N.M.R. (d$_6$-DMSO, δ): 1.18 (6H, d, J=6 Hz), 1.32 (9H, s), 3.62 (2H, broad s), 4.17–4.73 (5H, m), 5.17 (1H, d, J=4 Hz), 5.84 (1H, dd, J=4 and 8 Hz), 8.18 (2H, s), 9.63 (1H, d, J=8 Hz).

(51) 7-[2-Isopropoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp. 175° to 180° C. (dec.).

I.R. (Nujol): 3300, 3200, 1770, 1720, 1680, 1620, 1520 cm$^{-1}$.

(52) 7-[2-Methoxyimino-2-(5-amino-1,2,4-thiadiazol-3-yl)acetamido]-3-(5-carboxymethylthio-1,3,4-thiadiazol-2-yl)thiomethyl-3-cephem-4-carboxylic acid (syn isomer), mp. 150° to 155° C. (dec.).

I.R. (Nujol): 3350, 3250, 1780, 1720, 1680, 1620, 1530 cm$^{-1}$.

(53) 7-[2-Isopropoxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp. 170° to 175° C. (dec.).

I.R. (Nujol): 3350, 3250, 1780, 1680, 1620, 1530 cm$^{-1}$.

(54) 7-[2-Isopropoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp. 142° to 147° C. (dec.).

I.R. (Nujol): 3350, 3250, 1780, 1690, 1630, 1530 cm$^{-1}$.

(55) 7-[2-Isopropoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp. 165° to 170° C. (dec.).

I.R. (Nujol): 3300, 3200, 1775, 1710, 1670, 1625, 1525 cm$^{-1}$.

(56) 7-[2-Isopropoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp. 135° to 140° C. (dec.).

I.R. (Nujol): 3350, 3230, 1780, 1680, 1625, 1530 cm$^{-1}$.

(57) 7-[2-Methoxyimino-2-(5-amino-1,2,4-thiadiazol-3-yl)acetamido]-3-(5-trifluoromethyl-1,3,4-thiadiazol-2-yl)thiomethyl-3-cephem-4-carboxylic acid (syn isomer), mp. 150° to 155° C. (dec.).

I.R. (Nujol): 3300, 3200, 1770, 1670, 1620, 1520 cm$^{-1}$.

(58) 7-[2-Methoxyimino-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp. 205° to 210° C. (dec.).

I.R. (Nujol): 3300, 1765, 1710, 1680, 1620, 1550, 1520 cm$^{-1}$.

(59) 7-[2-Methoxyimino-2-(5-amino-1,2,4-thiadiazol-3-yl)acetamido]-3-(5-methylamino-1,3,4-thiadiazol-2-yl)thiomethyl-3-cephem-4-carboxylic acid (syn isomer), mp. 175° to 180° C. (dec.).

I.R. (Nujol): 3450, 3370, 3250, 1775, 1710, 1680, 1630, 1560 cm$^{-1}$.

(60) 7-[2-Methoxyimino-2-(5-amino-1,2,4-thiadiazol-3-yl)acetamido]-3-(5-amino-1,3,4-thiadiazol-2-yl)thiomethyl-3-cephem-4-carboxylic acid (syn isomer), mp. 165° to 170° C. (dec.).

I.R. (Nujol): 3350, 3210, 1770, 1670, 1620, 1520 cm$^{-1}$.

(61) 7-[2-Methoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp. 175° to 180° C. (dec.).

I.R. (Nujol): 3370, 3250, 1785, 1690, 1630, 1530 cm$^{-1}$.

(62) 7-[2-Methoxyimino-2-(5-amino-1,2,4-thiadiazol-3-yl)acetamido]-3-[1-{3-(acetamido)propyl}-1H-tetrazol-5-yl]thiomethyl-3-cephem-4-carboxylic acid (syn isomer), mp. 150° to 155° C. (dec.).

I.R. (Nujol): 3350, 3230, 1780, 1660, 1620, 1530 cm$^{-1}$.

(63) 7-[2-Methoxyimino-2-(5-amino-1,2,4-thiadiazol-3-yl)acetamido]-3-[1-{1-(acetamidomethyl)ethyl}-1H-tetrazol-5-yl]thiomethyl-3-cephem-4-carboxylic acid (syn isomer), mp. 160° to 165° C. (dec.).

I.R. (Nujol): 3350, 3250, 1780, 1660, 1620, 1530 cm$^{-1}$.

(64) 7-[2-Methoxyimino-2-(5-amino-1,2,4-thiadiazol-3-yl)acetamido]-3-[1-{1-(N-t-butoxycarbonylaminomethyl)ethyl}-1H-tetrazol-5-yl]thiomethyl-3-cephem-4-carboxylic acid (syn isomer), mp. 180° to 185° C. (dec.).

I.R. (Nujol): 3370, 3230, 1780, 1690, 1630, 1530 cm$^{-1}$.

(65) 7-[2-Methoxyimino-2-(5-amino-1,2,4-thiadiazol-3-yl)acetamido]-3-[1-{3-(N,N-dimethylamino)propyl}-1H-tetrazol-5-yl]thiomethyl-3-cephem-4-carboxylic acid (syn isomer), mp. 165° to 170° C. (dec.).

I.R. (Nujol): 3350, 3200, 1770, 1670, 1610, 1530 cm$^{-1}$.

(66) 7-[2-Methoxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp. 150° to 155° C. (dec.).

I.R. (Nujol): 3300, 3150, 1770, 1720, 1670, 1620, 1520 cm$^{-1}$.

N.M.R. (d$_6$-DMSO, δ): 2.93 (2H, t, J=9 Hz), 3.70 (2H, broad s), 3.92 (3H, s), 4.27 and 4.43 (2H, ABq, J=14 Hz), 4.45 (2H, t, J=9 Hz), 5.17 (1H, d, J=4 Hz), 5.83 (1H, dd, J=4 and 8 Hz), 8.18 (2H, s), 9.67 (1H, d, J=8 Hz).

(67) 7-[2-Methoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp. 123° to 125° C. (dec.).

I.R. (Nujol): 3300, 3200, 1750, 1720, 1680, 1620, 1520 cm$^{-1}$.

(68) 7-[2-Isopropoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp. 210° to 215° C. (dec.).

I.R. (Nujol): 3350, 3200, 1750, 1670, 1620, 1530 cm$^{-1}$.

(69) 7-[2-Isopropoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp. 195° to 200° C. (dec.).

I.R. (Nujol): 3350, 3250, 1775, 1680, 1620, 1530 cm$^{-1}$.

(70) 7-[2-Methoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp. 185° to 190° C. (dec.).

I.R. (Nujol): 3300, 3200, 1770, 1670, 1610, 1530 cm$^{-1}$.

(71) 7-[2-Methoxyimino-2-(5-amino-1,2,4-thiadiazol-3-yl)acetamido]-3-[1-{1-(aminomethyl)ethyl}-1H-tetrazol-5-yl]thiomethyl-3-cephem-4-carboxylic acid (syn isomer), mp. 190° to 195° C. (dec.).

I.R. (Nujol): 3350, 3230, 1770, 1670, 1620, 1530 cm$^{-1}$.

(72) 7-[2-Isopropoxyimino-2-(5-amino-1,2,4-thiadiazol-3-yl)acetamido]-3-cephem-4-carboxylic acid (syn isomer), mp. 208° to 213° C. (dec.).

I.R. (Nujol): 3400, 3350, 3250, 1770, 1660, 1630, 1610, 1520 cm$^{-1}$.

(73) 7-[2-Ethoxyimino-2-(5-amino-1,2,4-thiadiazol-3-yl)acetamido]-3-cephem-4-carboxylic acid (syn isomer), mp. 190° to 195° C. (dec.).

I.R. (Nujol): 3400, 3300, 3200, 1770, 1670, 1630, 1520 cm$^{-1}$.

EXAMPLE 12

To a cold solution of phosphorus pentachloride (3.12 g) in methylene chloride (37 ml) was added 2-methoxyimino-2-(5-amino-1,2,4-thiadiazol-3-yl)acetic acid (syn isomer) (1.01 g) at −15° C. and the mixture was stirred for 25 minutes at −10° to −13° C. and for 30 minutes at 0° to −3° C. On the other hand, a mixture of 7-amino-3-(1,3,4-thiadiazol-2-yl)thiomethyl-3-cephem-4-carboxylic acid (1.82 g) and trimethylsilylacetamide (5 g) in methylene chloride (25 ml) was warmed to make a clear solution and then cooled to −10° C. The solution was added to the above activated mixture and the mixture was stirred for 0.5 hour at −5° to 0° C. The reaction mixture was filtered and to the filtrate was added an aqueous solution of sodium bicarbonate (80 ml). The mixture was stirred at ambient temperature and methylene chloride was distilled off. The aqueous layer was adjusted to pH 1 with 10% hydrochloric acid and subjected to column chromatography on Diaion HP-20 resin (200 ml) (Trademark: prepared by Mitsubishi Chemical Industries Ltd.) using successively water, 20% aqueous methanol (500 ml) and 40% aqueous methanol (500 ml) and the eluate was lyophilized to give 7-[2-methoxyimino-2-(5-phosphonoamino-1,2,4-thiadiazol-3-yl)acetamido]-3-(1,3,4-thiadiazol-2-yl)thiomethyl-3-cephem-4-carboxylic acid (syn isomer) (440 mg), mp. 140° to 145° C. (dec.).

I.R. (Nujol): 3180, 1765, 1670, 1515 cm$^{-1}$.

N.M.R. (d$_6$-DMSO, δ): 3.72 (2H, broad s), 3.93 (3H, s), 4.32 and 4.57 (2H, ABq, J=13 Hz), 5.17 (1H, d, J=5 Hz), 5.85 (1H, dd, J=5 and 8 Hz), 9.58 (1H, s), 9.63 (1H, d, J=8 Hz).

EXAMPLE 13

Preparation of 7-[2-methoxyimino-2-(5-amino-1,2,4-thiadiazol-3-yl)acetamido]-3-cephem-4-carboxylic acid (syn isomer).

In a mixture of tetrahydrofuran (20 ml), methanol (10 ml), acetic acid (0.25 ml) and water (2.5 ml) was dissolved 4-nitrobenzyl 7-[2-methoxyimino-2-(5-amino-1,2,4-thiadiazol-3-yl)acetamido]-3-cephem-4-carboxylate (syn isomer) (0.87 g) and thereto was added 5% palladium-carbon (0.87 g). The resulting mixture was shaken under a hydrogen atmosphere at atmospheric pressure and ambient temperature for 6 hours. The reaction mixture was filtered and the filtrate was evaporated to dryness. The residue was dissolved in an aqueous solution of sodium bicarbonate and the solution was washed with ethyl acetate. The aqueous layer was adjusted to pH 2 with 10% hydrochloric acid and extracted with ethyl acetate. The extract was dried over magnesium sulfate and evaporated to dryness. The residue was triturated with diethyl ether to give the title compound (350 mg), mp. 190° to 195° C. (dec.).

I.R. (Nujol): 3350, 1775, 1680, 1630, 1530 cm$^{-1}$.

N.M.R. (d$_6$-DMSO, δ): 3.60 (2H, broad s), 3.93 (3H, s), 5.10 (1H, d, J=4 Hz), 5.85 (1H, 2d, J=4,8 Hz), 6.50 (1H, t, J=4 Hz), 8.10 (2H, s), 9.57 (1H, d, J=8 Hz).

EXAMPLE 14

A mixture of 4-nitrobenzyl 7-[2-ethoxyimino-2-(5-amino-1,2,4-thiadiazol-3-yl)acetamido]-3-cephem-4-carboxylate (syn isomer) (5.0 g) and 10% palladium on carbon (2.5 g) in 70% aqueous tetrahydrofuran (75 ml) was stirred under hydrogen atmosphere for 3 hours at ambient temperature. The catalyst was removed by filtration and the filtrate was concentrated to third volume. The residue was extracted with ethyl acetate and transferred into an aqueous solution of sodium bicarbonate. The aqueous layer was acidified to pH 3 with 10% hydrochloric acid and extracted with ethyl acetate. The extract was dried over magnesium sulfate and concentrated to 10 ml under reduced pressure. The resultant precipitates were collected, washed with ethyl acetate and dried to give 7-[2-ethoxyimino-2-(5-amino-1,2,4-thiadiazol-3-yl)acetamido]-3-cephem-4-carboxylic acid (syn isomer) (1.33 g), mp. 190° to 195° C. (dec.).

I.R. (Nujol): 3400, 3300, 3200, 1770, 1670, 1630, 1520 cm$^{-1}$.

N.M.R. (d$_6$-DMSO, δ): 1.23 (3H, t, J=7 Hz), 3.58 (2H, broad s), 4.17 (2H, q, J=7 Hz), 5.07 (1H, d, J=4 Hz), 5.83 (1H, dd, J=4 and 8 Hz), 6.45 (1H, t, J=4 Hz), 8.05 (2H, s), 9.50 (1H, d, J=8 Hz).

EXAMPLE 15

The following compounds were obtained according to similar manners to those of Examples 13 and 14.

(1) 7-[2-Methoxyimino-2-(5-formamido-1,2,4-thiadiazol-3-yl)acetamido]-3-(1-methyl-1H-tetrazol-5-ylthiomethyl)-3-cephem-4-carboxylic acid (syn isomer), mp. 170° to 175° C. (dec.).

I.R. (Nujol): 3300, 1780, 1680 cm$^{-1}$.

(2) 7-[2-Methoxyimino-2-(5-amino-1,2,4-thiadiazol-3-yl)acetamido]-3-(1-methyl-1H-tetrazol-5-ylthiomethyl)-3-cephem-4-carboxylic acid (syn isomer), mp. 170° to 175° C. (dec.).

I.R. (Nujol): 3300, 1770, 1660, 1610, 1520 cm$^{-1}$.

(3) 7-[2-Methoxyimino-2-(5-amino-1,2,4-thiadiazol-3-yl)acetamido]cephalosporanic acid (syn isomer), mp. 180° to 185° C. (dec.).

I.R. (Nujol): 3350, 1780, 1730, 1680, 1620, 1530 cm$^{-1}$.

(4) 7-[2-Methoxyimino-2-(5-amino-1,2,4-thiadiazol-3-yl)acetamido]-3-carbamoyloxymethyl-3-cephem-4-carboxylic acid (syn isomer), mp. 185° to 190° C. (dec.).

I.R. (Nujol): 3350, 1780, 1720, 1680, 1620, 1530 cm$^{-1}$.

(5) 7-[2-Methoxyimino-2-(5-amino-1,2,4-thiadiazol-3-yl)acetamido]-2-methyl-3-cephem-4-carboxylic acid (syn isomer), mp. 175° to 180° C. (dec.).

I.R. (Nujol): 3350, 1775, 1675, 1630, 1530 cm$^{-1}$.

(6) 7-[2-Methoxyimino-2-(5-amino-1,2,4-thiadiazol-3-yl)acetamido]-3-(5-methyl-1,3,4-thiadiazol-2-ylthiomethyl)-3-cephem-4-carboxylic acid (syn isomer), mp. 175° to 180° C. (dec.).

I.R. (Nujol): 3350, 1780, 1680, 1625, 1530 cm$^{-1}$.

(7) 7-[2-Methoxyimino-2-(5-amino-1,2,4-thiadiazol-3-yl)acetamido]-3-(1,3,4-thiadiazol-2-ylthiomethyl)-3-cephem-4-carboxylic acid (syn isomer), mp. 172° to 177° C. (dec.).

I.R. (Nujol): 3350, 1775, 1680, 1625, 1530 cm$^{-1}$.

(8) 7-[2-Methoxyimino-2-(5-amino-1,2,4-thiadiazol-3-yl)acetamido]-3-(1-allyl-1H-tetrazol-5-ylthiomethyl)-3-cephem-4-carboxylic acid (syn isomer), mp. 170° to 172° C. (dec.).

I.R. (Nujol): 3350, 1780, 1680, 1625, 1530 cm$^{-1}$.

(9) 7-[2-Isopropoxyimino-2-(5-amino-1,2,4-thiadiazol-3-yl)acetamido]-3-cephem-4-carboxylic acid (syn isomer), mp. 208° to 213° C. (dec.).

I.R. (Nujol): 3400, 3350, 3250, 1770, 1660, 1630, 1610, 1520 cm$^{-1}$.

N.M.R. (d$_6$-DMSO, δ): 1.27 (6H, d, J=6 Hz), 3.57 (2H, d, J=4 Hz), 4.17-4.60 (1H, m), 5.07 (1H, d, J=4 Hz), 5.83 (1H, dd, J=4 and 8 Hz), 6.43 (1H, t, J=4 Hz), 8.07 (2H, s), 9.45 (1H, d, J=8 Hz).

(10) 7-[2-Isopropoxyimino-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp. 140° to 145° C. (dec.).

I.R. (Nujol): 3300, 1780, 1670, 1620, 1530 cm$^{-1}$.

(11) 7-[2-Isopropoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp. 175° to 180° C. (dec.).

I.R. (Nujol): 3300, 3200, 1770, 1720, 1680, 1620, 1520 cm$^{-1}$.

(12) 7-[2-Methoxyimino-2-(5-amino-1,2,4-thiadiazol-3-yl)acetamido]-3-(5-carboxymethylthio-1,3,4-thiadiazol-2-yl)thiomethyl-3-cephem-4-carboxylic acid (syn isomer), mp. 150° to 155° C. (dec.).

I.R. (Nujol): 3350, 3250, 1780, 1720, 1680, 1620, 1530 cm$^{-1}$.

(13) 7-[2-Isopropoxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp. 170° to 175° C. (dec.).

I.R. (Nujol): 3350, 3250, 1780, 1680, 1620, 1530 cm$^{-1}$.

(14) 7-[2-Isopropoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp. 142° to 147° C. (dec.).

I.R. (Nujol): 3350, 3250, 1780, 1690, 1630, 1530 cm$^{-1}$.

(15) 7-[2-Isopropoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp. 165° to 170° C. (dec.).

I.R. (Nujol): 3300, 3200, 1775, 1710, 1670, 1625, 1525 cm$^{-1}$.

(16) 7-[2-Isopropoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp. 135° to 140° C. (dec.).

I.R. (Nujol): 3350, 3230, 1780, 1680, 1625, 1530 cm$^{-1}$.

(17) 7-[2-Methoxyimino-2-(5-amino-1,2,4-thiadiazol-3-yl)acetamido]-3-(5-trifluoromethyl-1,3,4-thiadiazol-2-yl)thiomethyl-3-cephem-4-carboxylic acid (syn isomer), mp. 150° to 155° C. (dec.).

I.R. (Nujol): 3300, 3200, 1770, 1670, 1620, 1520 cm$^{-1}$.

(18) 7-[2-Methoxyimino-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp. 205° to 210° C. (dec.).

I.R. (Nujol): 3300, 1765, 1710, 1680, 1620, 1550, 1520 cm$^{-1}$.

(19) 7-[2-Methoxyimino-2-(5-amino-1,2,4-thiadiazol-3-yl)acetamido]-3-(5-methylamino-1,3,4-thiadiazol-2-yl)thiomethyl-3-cephem-4-carboxylic acid (syn isomer), mp. 175° to 180° C. (dec.).

I.R. (Nujol): 3450, 3370, 3250, 1775, 1710, 1680, 1630, 1560 cm$^{-1}$.

(20) 7-[2-Methoxyimino-2-(5-amino-1,2,4-thiadiazol-3-yl)acetamido]-3-(5-amino-1,3,4-thiadiazol-2-yl)thiomethyl-3-cephem-4-carboxylic acid (syn isomer), mp. 165° to 170° C. (dec.).

I.R. (Nujol): 3350, 3210, 1770, 1670, 1620, 1520 cm$^{-1}$.

(21) 7-[2-Methoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp. 175° to 180° C. (dec.).

I.R. (Nujol): 3370, 3250, 1785, 1690, 1630, 1530 cm$^{-1}$.

(22) 7-[2-Methoxyimino-2-(5-amino-1,2,4-thiadiazol-3-yl)acetamido]-3-[1-{3-(acetamido)propyl}-1H-tetrazol-5-yl]thiomethyl-3-cephem-4-carboxylic acid (syn isomer), mp. 150° to 155° C. (dec.).

I.R. (Nujol): 3350, 3230, 1780, 1660, 1620, 1530 cm$^{-1}$.

(23) 7-[2-Methoxyimino-2-(5-amino-1,2,4-thiadiazol-3-yl)acetamido]-3-[1-{1-(acetamidomethyl)ethyl}-1H-tetrazol-5-yl]thiomethyl-3-cephem-4-carboxylic acid (syn isomer), mp. 160° to 165° C. (dec.).

I.R. (Nujol): 3350, 3250, 1780, 1660, 1620, 1530 cm$^{-1}$.

(24) 7-[2-Methoxyimino-2-(5-amino-1,2,4-thiadiazol-3-yl)acetamido]-3-[1-{1-(N-t-butoxycarbonylaminomethyl)ethyl}-1H-tetrazol-5-yl]thiomethyl-3-cephem-4-carboxylic acid (syn isomer), mp. 180° to 185° C. (dec.).

I.R. (Nujol): 3370, 3230, 1780, 1690, 1630, 1530 cm$^{-1}$.

(25) 7-[2-Methoxyimino-2-(5-amino-1,2,4-thiadiazol-3-yl)acetamido]-3-[1-{3-(N,N-dimethylamino)propyl}-1H-tetrazol-5-yl]thiomethyl-3-cephem-4-carboxylic acid (syn isomer), mp. 165° to 170° C. (dec.).

I.R. (Nujol): 3350, 3200, 1770, 1670, 1610, 1530 cm$^{-1}$.

(26) 7-[2-Methoxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp. 150° to 155° C. (dec.).

I.R. (Nujol): 3300, 3150, 1770, 1720, 1670, 1620, 1520 cm$^{-1}$.

(27) 7-[2-Methoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp. 123° to 125° C. (dec.).

I.R. (Nujol): 3300, 3200, 1750, 1720, 1680, 1620, 1520 cm$^{-1}$.

(28) 7-[2-Isopropoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp. 210° to 215° C. (dec.).

I.R. (Nujol): 3350, 3200, 1750, 1670, 1620, 1530 cm$^{-1}$.

(29) 7-[2-Isopropoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp. 195° to 200° C. (dec.).

I.R. (Nujol): 3350, 3250, 1775, 1680, 1620, 1530 cm$^{-1}$.

(30) 7-[2-Methoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp. 185° to 190° C. (dec.).

I.R. (Nujol): 3300, 3200, 1770, 1670, 1610, 1530 cm$^{-1}$.

(31) 7-[2-Methoxyimino-2-(5-amino-1,2,4-thiadiazol-3-yl)acetamido]-3-[1-{1-(aminomethyl)ethyl}-1H-tetrazol-5-yl]thiomethyl-3-cephem-4-carboxylic acid (syn isomer), mp. 190° to 195° C. (dec.).

I.R. (Nujol): 3350, 3230, 1770, 1670, 1620, 1530 cm$^{-1}$.

(32) 7-[2-Methoxyimino-2-(5-phosphonoamino-1,2,4-thiadiazol-3-yl)acetamido]-3-(1,3,4-thiadiazol-2-yl)thiomethyl-3-cephem-4-carboxylic acid (syn isomer), mp. 140° to 145° C. (dec.).

I.R. (Nujol): 3180, 1765, 1670, 1515 cm$^{-1}$.

(33) 7-[2-Ethoxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

I.R. (Nujol): 3350, 3230, 1775, 1680, 1620, 1530 cm$^{-1}$.

(34) 7-[2-Isopropoxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 145° to 150° C. (dec.).

I.R. (Nujol): 3370, 3230, 1780, 1680, 1625, 1530 cm$^{-1}$.

(35) 7-[2-Isopropoxyimino-2-(5-amino-1,2,4-thiadiazol-3-yl)acetamido]cephalosporanic acid (syn isomer), mp 150° to 155° C. (dec.)

I.R. (Nujol): 3300, 1780, 1725, 1660, 1520 cm$^{-1}$.

(36) 7-[2-Propoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 133° C. (dec.)

I.R. (Nujol): 3380, 3230, 1780, 1680, 1625, 1530 cm$^{-1}$.

(37) 7-[2-Methoxyimino-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp 150° to 155° C. (dec.)

I.R. (Nujol): 3350, 3250, 1780, 1670 cm$^{-1}$.

(38) 7-[2-Methoxyimino-2-(5-amino-1,2,4-thiadiazol-3-yl)acetamido]-3-(5-allylthio-1,3,4-thiadiazol-2-yl)thiomethyl-3-cephem-4-carboxylic acid (syn isomer). mp 160° to 165° C. (dec.)

I.R. (Nujol): 3350, 3250, 1780, 1680, 1620 cm$^{-1}$.

(39) 7-[2-Methoxyimino-2-(5-amino-1,2,4-thiadiazol-3-yl)acetamido]-3-acetylthiomethyl-3-cephem-4-carboxylic acid (syn isomer). mp 178° to 182° C. (dec.)

I.R. (Nujol): 3350, 3250, 1780, 1680, 1620 cm$^{-1}$.

(40) 7-[2-Methoxyimino-2-(5-amino-1,2,4-thiadiazol-3-yl)acetamido]-3-pyrazinylthiomethyl-3-cephem-4-carboxylic acid (syn isomer). mp 170° to 174° C. (dec.)

I.R. (Nujol): 3350, 3250, 1780, 1680, 1620, 1530 cm$^{-1}$.

(41) 7-[2-Methoxyimino-2-(5-amino-1,2,4-thiadiazol-3-yl)acetamido]-3-(2-thiazolin-2-yl)thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

(42) 7-[2-Methoxymino-2-(5-amino-1,2,4-thiadiazol-3-yl)acetamido]-3-(tetrazolo[1,5-b]pyridazin-6-yl)thiomethyl-3-cephem-4-carboxylic acid (syn isomer). mp 175° to 180° C. (dec.)

I.R. (Nujol): 3400, 3250, 1885, 1725, 1670, 1640, 1540 cm$^{-1}$.

(43) 7-[2-Methoxyimino-2-(5-amino-1,2,4-thiadiazol-3-yl)acetamido]-3-[1-{2-(N-t-butoxycarbonylamino)ethyl]-1H-tetrazol-5-yl]thiomethyl-3-cephem-4-carboxylic acid (syn isomer). mp 200° to 205° C. (dec.)

I.R. (Nujol): 3300, 1780, 1700, 1680, 1620, 1520 cm$^{-1}$.

(44) 7-[2-Methoxyimino-2-(5-amino-1,2,4-thiadiazol-3-yl)acetamido]-3-(1-propyl-1H-tetrazol-5-yl)thiomethyl-3-cephem-4-carboxylic acid (syn isomer). mp 155° to 160° C. (dec.)

I.R. (Nujol): 3350, 3250, 1780, 1680, 1630, 1530 cm$^{-1}$.

(45) 7-[2-Methoxyimino-2-(5-amino-1,2,4-thiadiazol-3-yl)acetamido]-3-[1-(3-methoxypropyl)-1H-tetrazol-5-yl]thiomethyl-3-cephem-4-carboxylic acid (syn isomer). mp 165° to 167° C. (dec.)

I.R. (Nujol): 3350, 3250, 1780, 1680, 1620, 1530 cm$^{-1}$.

(46) 7-[2-Methoxyimino-2-(5-amino-1,2,4-thiadiazol-3-yl)acetamido]-3-(3-methyl-1,2,4-thiadiazol-5-yl)thiomethyl-3-cephem-4-carboxylic acid (syn isomer). mp 178° to 182° C. (dec.)

I.R. (Nujol): 3350, 3250, 1780, 1680, 1630, 1530 cm$^{-1}$.

(47) 7-[2-Methoxyimino-2-(5-amino-1,2,4-thiadiazol-3-yl)acetamido]-3-(5-methoxymethyl-1,3,4-thiadiazol-2-yl)thiomethyl-3-cephem-4-carboxylic acid (syn isomer). mp 170° to 174° C. (dec.)

I.R. (Nujol): 3350, 3250, 1780, 1680, 1630, 1530 cm$^{-1}$.

(48) 7-[2-Methoxyimino-2-(5-amino-1,2,4-thiadiazol-3-yl)acetamido]-3-(5-methylthiomethyl-1,3,4-thiadiazol-2-yl)thiomethyl-3-cephem-4-carboxylic acid (syn isomer). mp 173° to 175° C. (dec.)

I.R. (Nujol): 3350, 3250, 1780, 1680, 1630, 1530 cm$^{-1}$.

(49) 7-[2-Methoxyimino-2-(5-amino-1,2,4-thiadiazol-3-yl)acetamido]-3-(4-propyl-4H-1,2,4-triazol-3-yl)thiomethyl-3-cephem-4-carboxylic acid (syn isomer). mp 182° to 184° C. (dec.)

I.R. (Nujol): 3350, 3250, 1780, 1680, 1620, 1530 cm$^{-1}$.

(50) 7-[2-Methoxyimino-2-(5-amino-1,2,4-thiadiazol-3-yl)acetamido]-3-(1-methylthiomethyl-1H-tetrazol-5-yl)thiomethyl-3-cephem-4-carboxylic acid (syn isomer). mp 175° to 178° C. (dec.)

I.R. (Nujol): 3350, 3250, 1780, 1680, 1620, 1530 cm$^{-1}$.

(51) 7-[2-Methoxyimino-2-(5-amino-1,2,4-thiadiazol-3-yl)acetamido]-3-(1-isopropyl-1H-tetrazol-5-yl)thiomethyl-3-cephem-4-carboxylic acid (syn isomer). mp 180° to 182° C. (dec.)

I.R. (Nujol): 3350, 3250, 1780, 1680, 1630, 1530 cm$^{-1}$.

(52) 7-[2-Methoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer). mp 170° to 175° C. (dec.)

I.R. (Nujol): 3350, 3250, 1780, 1680, 1625, 1530 cm$^{-1}$.

(53) 7-[2-Methoxyimino-2-(5-amino-1,2,4-thiadiazol-3-yl)acetamido]-3-[5-(2-hydroxyethyl)-1,3,4-thiadiazol-2-yl]thiomethyl-3-cephem-4-carboxylic acid (syn isomer). mp 175° to 180° C. (dec.)

I.R. (Nujol): 3350, 3250, 1780, 1680, 1630, 1530 cm$^{-1}$.

(54) 7-[2-Methoxyimino-2-(5-amino-1,2,4-thiadiazol-3-yl)acetamido]-3-(5-propyl-1,3,4-thiadiazol-2-yl)thiomethyl-3-cephem-4-carboxylic acid (syn isomer). mp 177° to 180° C. (dec.)

I.R. (Nujol): 3350, 3250, 1780, 1680, 1630, 1530 cm$^{-1}$.

(55) 7-[2-Methoxyimino-2-(5-amino-1,2,4-thiadiazol-3-yl)acetamido]-3-(5-hydroxymethyl-1,3,4-thiadiazol-2-yl)thiomethyl-3-cephem-4-carboxylic acid (syn isomer). mp 165° to 170° C. (dec.)

I.R. (Nujol): 3350, 3250, 1780, 1680, 1620, 1530 cm$^{-1}$.

(56) 7-[2-Methoxyimino-2(5-amino-1,2,4-thiadiazol-3-yl)acetamido]-3-(5-methanesulfonamidomethyl-1,3,4-thiadiazol-2-yl)thiomethyl-3-cephem-4-carboxylic acid (syn isomer). mp 170° to 175° C. (dec.)

I.R. (Nujol): 3350, 3250, 1780, 1680, 1620, 1530 cm$^{-1}$.

(57) 7-[2-Methoxyimino-2-(5-amino-1,2,4-thiadiazol-3-yl)acetamido]-3-(3-allylthio-1,2,4-thiadiazol-5-yl)thiomethyl-3-cephem-4-carboxylic acid (syn isomer). mp 170° to 173° C. (dec.)

I.R. (Nujol): 3350, 3250, 1780, 1680, 1620, 1530 cm$^{-1}$.

(58) 7-[2-Methoxyimino-2-(5-amino-1,2,4-thiadiazol-3-yl)acetamido]-3-(5-mesylmethyl-1,3,4-thiadiazol-2-yl)thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

(59) Sodium 7-[2-methoxyimino-2-(5-amino-1,2,4-thiadiazol-3-yl)acetamido]-3-(1-sulfonatomethyl-1H-tetrazol-5-yl)thiomethyl-3-cephem-4-carboxylic acid (syn isomer). mp 205° to 210° C. (dec.)

I.R. (Nujol): 3350, 3250, 1780, 1680, 1530 cm$^{-1}$.

(60) 7-[2-Methoxyimino-2-(5-amino-1,2,4-thiadiazol-3-yl)acetamido]-3-(4-methyl-4H-1,2,4-triazol-3-yl)thiomethyl-3-cephem-4-carboxylic acid (syn isomer). mp 180° to 185° C. (dec.)

I.R. (Nujol): 3350, 3250, 1780, 1680, 1620, 1530 cm$^{-1}$.

(61) 7-[2-Methoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer). mp 185° to 190° C. (dec.)

I.R. (Nujol): 3350, 3250, 1780, 1680, 1620, 1530 cm$^{-1}$.

(62) 7-[2-Methoxyimino-2-(5-amino-1,2,4-thiadiazol-3-yl)acetamido]-3-[4-(3-methoxypropyl)-4H-1,2,4-triazol-3-yl]thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

(63) 7-[2-Methoxyimino-2-(5-amino-1,2,4-thiadiazol-3-yl)acetamido]-3-[5-(2-aminoethyl)-1,3,4-thiadiazol-2-yl]thiomethyl-3-cephem-4-carboxylic acid (syn isomer). mp 205° to 210° C. (dec.)

I.R. (Nujol): 3200, 1770, 1670, 1620, 1530 cm$^{-1}$.

(64) 7-[2-Methoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 210° to 215° C. (dec.)

I.R. (Nujol): 3350, 3200, 1770, 1680, 1620 cm$^{-1}$.

(65) 7-[2-Methoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 200° to 205° C. (dec.)

I.R. (Nujol): 3350, 3200, 1775, 1670, 1620, 1530 cm$^{-1}$.

(66) 7-[2-Ethoxyimino-2-(5-amino-1,2,4-thiadiazol-3-yl)acetamido]cephalosporanic acid (syn isomer). mp 140° to 156° C. (dec.)

I.R. (Nujol): 3370, 3250, 1780, 1730, 1680, 1620, 1530, 1380, 1240, 1040 cm$^{-1}$.

(67) 7-[2-Ethoxyimino-2-(5-amino-1,2,4-thiadiazol-3-yl)acetamido]-3-[1-{3-(N-t-butoxycarbonylamino)-propyl}-1H-tetrazol-5-yl]thiomethyl-3-cephem-4-carboxylic acid (syn isomer). mp 183° to 188° C. (dec.)

I.R. (Nujol): 3370, 3240, 1780, 1690, 1630, 1530, 1380, 1260, 1170, 1040 cm$^{-1}$.

(68) 7-[2-Ethoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer).

I.R. (Nujol): 3360, 3240, 1780, 1690, 1630, 1530, 1375, 1250, 1170, 1040 cm$^{-1}$.

(69) 7-[2-Ethoxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 156° to 159° C. (dec.)

I.R. (Nujol): 3360, 3250, 1780, 1680, 1625, 1380, 1080, 1040 cm$^{-1}$.

(70) 7-[2-Ethoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer). mp 177° to 180° C. (dec.)

I.R. (Nujol): 3380, 3250, 1775, 1670, 1620, 1535, 1380, 1040 cm$^{-1}$.

(71) 7-[2-Ethoxyimino-2-(5-amino-1,2,4-thiadiazol-3-yl)acetamido]-3-(1-allyl-1H-tetrazol-5-yl)thiomethyl-3-cephem-4-carboxylic acid (syn isomer). mp 160° to 165° C. (dec.)

I.R. (Nujol): 3380, 3250, 1780, 1680, 1630, 1530, 1380, 1040 cm$^{-1}$.

(72) 7-[2-Ethoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer). mp 180° to 185° C. (dec.)

I.R. (Nujol): 3350, 3240, 1780, 1680, 1620, 1530, 1380, 1040 cm$^{-1}$.

(73) 7-[2-Ethoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 198° to 205° C. (dec.)

I.R. (Nujol): 3350, 3250, 1775, 1680, 1620, 1535, 1380, 1040 cm$^{-1}$.

(74) 7-[2-Ethoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer). mp 170° to 173° C. (dec.)

I.R. (Nujol): 3350, 3240, 1780, 1675, 1625, 1530, 1380, 1040, 720 cm$^{-1}$.

(75) 7-[2-Methoxyimino-2-(5-amino-1,2,4-thiadiazol-3-yl)acetamido]-3-(4-allyl-4H-1,2,4-triazol-3-yl)thiomethyl-3-cephem-4-carboxylic acid (syn isomer). mp 185° to 190° C. (dec.)

I.R. (Nujol): 3350, 3250, 1780, 1680, 1625, 1530 cm$^{-1}$.

(76) 7-[2-Methoxyimino-2-(5-amino-1,2,4-thiadiazol-3-yl)acetamido]-3-(3-methoxycarbonyl-1,2,4-thiadiazol-5-yl)thiomethyl-3-cephem-4-carboxylic acid (syn isomer). mp 180° to 185° C. (dec.)

I.R. (Nujol): 3350, 3250, 1780, 1740, 1680, 1620, 1530 cm$^{-1}$.

(77) 7-[2-Methoxyimino-2-(5-amino-1,2,4-thiadiazol-3-yl)acetamido]-3-(3-carboxy-1,2,4-thiadiazol-5-yl)thiomethyl-3-cephem-4-carboxylic acid (syn isomer). mp 175° to 180° C. (dec.)

I.R. (Nujol): 3350, 3250, 1780, 1730, 1680, 1620, 1530 cm$^{-1}$.

(78) 7-[2-Ethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer). mp 182° to 185° C. (dec.).

I.R. (Nujol): 3350, 3200, 1770, 1670, 1620, 1530, 1380, 1040 cm$^{-1}$.

(79) 7-[2-Ethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 195° to 210° C. (dec.).

I.R. (Nujol): 3340, 3210, 1770, 1675, 1620, 1530, 1380, 1040 cm$^{-1}$.

EXAMPLE 16

A mixture of 7-[2-methoxyimino-2-(5-amino-1,2,4-thiadiazol-3-yl)acetamido]cephalosporanic acid (syn isomer) (3.5 g), pyrazinethiol (1.1 g) and sodium bicarbonate (1.3 g) in pH 6.86 phosphate buffer solution (150 ml) was stirred for 2 hours at 70° C. The mixture was cooled in an ice bath, acidified with 10% hydrochloric acid and extracted with ethyl acetate. The extract was dried over magnesium sulfate and concentrated to 15 ml in vacuo. A resulting precipitate was collected by filtration, washed with ethyl acetate and dried to give crude 7-[2-methoxyimino-2-(5-amino-1,2,4-thiadiazol-3-yl)acetamido]-3-pyrazinylthiomethyl-3-cephem-4-carboxylic acid (syn isomer) (1.8 g). The crude product was dissolved in acetone, treated with activated charcoal powder and evaporated to dryness. The residue was dissolved in an aqueous solution of sodium bicarbonate and reprecipitated with an addition of 10% hydrochloric acid to give pure object compound (1.1 g). mp 170° to 174° C. (dec.)

I.R. (Nujol): 3350, 3250, 1780, 1680, 1620, 1530 cm$^{-1}$.

N.M.R. (d$_6$-DMSO, δ): 3.52 and 3.70 (2H, ABq, J=18 Hz), 3.97 (3H, s), 4.05 and 4.57 (2H, ABq, J=13 Hz), 5.13 (1H, d, J=4 Hz), 5.80 (1H, dd, J=4 and 8 Hz), 8.12 (2H, s), 8.3–8.6 (3H, m), 9.55 (1H, d, J=8 Hz).

EXAMPLE 17

A mixture of 7-[2-methoxyimino-2-(5-amino-1,2,4-thiadiazol-3-yl)acetamido]cephalosporanic acid (syn isomer) (3.0 g), tetrazolo[1,5-b]pyridazine-6-thiol (1.3 g) and sodium bicarbonate (1.1 g) in pH 6.86 phosphate buffer solution (130 ml) was stirred for 3 hours at 70° C. The mixture was cooled in an ice bath, acidified to pH 2 with 10% hydrochloric acid and extracted with ethyl acetate. The extract was dried over magnesium sulfate and concentrated to 15 ml in vacuo. A resulting precipitate was collected by filtration, washed with ethyl acetate and dried to give crude 7-[2-methoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer) (2.5 g). The crude product was dissolved in aqueous acetone, treated with activated charcoal powder and evaporated to dryness. The residue was dissolved in an aqueous solution of sodium bicarbonate and reprecipitated with an addition of 10% hydrochloric acid to give pure object compound (1.15 g). mp 175° to 180° C. (dec.)

I.R. (Nujol): 3400, 3250, 1885, 1725, 1670, 1640, 1540 cm$^{-1}$.

N.M.R. (d$_6$-DMSO, δ): 3.62 and 3.82 (2H, ABq, J=18 Hz), 3.92 (3H, s), 4.20 and 4.62 (2H, ABq, J=14 Hz), 5.14 (1H, d, J=4 Hz), 5.80 (1H, dd, J=4 and 8 Hz), 7.72 (1H, d, J=8 Hz), 8.10 (2H, s), 8.56 (1H, d, J=8 Hz), 9.56 (1H, d, J=8 Hz).

EXAMPLE 18

A mixture of 7-[2-methoxyimino-2-(5-amino-1,2,4-thiadiazol-3-yl)acetamido]cephalosporanic acid (syn isomer) (3.5 g), 1-[2-(N-t-butoxycarbonylamino)ethyl]-1H-tetrazole-5-thiol (2.45 g) and sodium bicarbonate (1.3 g) in pH 6.86 phosphate buffer solution (150 ml) was stirred for 3 hours at 70° C. The mixture was cooled in an ice bath, washed with ethyl acetate, acidified to pH 2 with 10% hydrochloric acid and extracted with ethyl acetate. The extract was dried over magnesium sulfate and concentrated to 10 ml in vacuo. A resulting precipitate was collected by filtration, washed with ethyl acetate and diethyl ether and dried to give 7-[2-methoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer) (2.0 g). mp 200° to 205° C. (dec.)

I.R. (Nujol): 3300, 1780, 1700, 1680, 1620, 1520 cm$^{-1}$.

N.M.R. (d$_6$-DMSO, δ): 1.27 (9H, s), 3.28 (2H, m), 3.63 (2H, broad s), 3.87 (3H, s), 4.27 (4H, broad s), 5.07 (1H, d, J=4 Hz), 5.75 (1H, dd, J=4 and 8 Hz), 8.10 (2H, s), 9.50 (1H, d, J=8 Hz).

EXAMPLE 19

A mixture of 7-[2-methoxyimino-2-(5-amino-1,2,4-thiadiazol-3-yl)acetamido]cephalosporanic acid (syn isomer) (3.5 g), sodium (5-mercapto-1H-tetrazol-1-yl)methanesulfonate (2.18 g) and sodium bicarbonate (1.3 g) in pH 6.86 phosphate buffer solution (150 ml) was stirred for 3 hours at 70° C. The mixture was cooled in an ice bath, adjusted to pH 3 with 10% hydrochloric acid and washed with ethyl acetate. The aqueous solution was subjected to column chromatography on non ion adsorption resin (Diaion HP 20) (Trademark: prepared by Mitsubishi Chemical Industries). The column was washed with water and eluted with 30% aqueous methanol. The eluate was evaporated to remove methanol and then lyophilized to give sodium 7-[2-methoxyimino-2-(5-amino-1,2,4-thiadiazol-3-yl)acetamido]-3-(1-sulfonatomethyl-1H-tetrazol-5-yl)thiomethyl-3-cephem-4-carboxylic acid (syn isomer) (0.67 g). mp 205° to 210° C. (dec.)

I.R. (Nujol): 3350, 3250, 1780, 1680, 1530 cm$^{-1}$.

N.M.R. (d$_6$-DMSO, δ): 3.63 (2H, broad s), 3.88 (3H, s), 4.27 and 4.33 (2H, ABq, J=14 Hz), 4.98 (2H, s), 5.07 (1H, d, J=4 Hz), 5.77 (1H, dd, J=4 and 8 Hz), 9.55 (1H, d, J=8 Hz).

EXAMPLE 20

A mixture of 7-[2-methoxyimino-2-(5-amino-1,2,4-thiadiazol-3-yl)acetamido]cephalosporanic acid (syn isomer) (3.5 g), disodium (5-sulfido-1H-tetrazol-1-yl)acetate (2.0 g) and sodium bicarbonate (1.3 g) in pH 6.8 phosphate buffer solution (150 ml) was stirred for 3.5 hours at 70° C. The reaction mixture was cooled in an ice bath, mixed with ethyl acetate and adjusted to pH 3 with 10% hydrochloric acid. The aqueous layer was separated, mixed with ethyl acetate and the mixture was adjusted to pH 1 with 10% hydrochloric acid. The ethyl acetate layer was dried over magnesium sulfate and evaporated to dryness. The residue was triturated with diethyl ether to give 7-[2-methoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer) (1.68 g), mp. 123° to 125° C. (dec.).

I.R. (Nujol): 3300, 3200, 1750, 1720, 1680, 1620, 1520 cm$^{-1}$.

N.M.R. (d$_6$-DMSO, δ): 3.72 (2H, broad s), 3.97 (3H, s), 4.27 and 4.50 (2H, ABq, J=13 Hz), 5.13 (1H, d, J=4 Hz), 5.33 (2H, s), 5.83 (1H, dd, J=4 and 8 Hz), 8.13 (2H, s), 9.60 (1H, d, J=8 Hz).

EXAMPLE 21

The following compounds were obtained according to similar manners to those of Examples 16 to 20.

(1) 7-[2-Methoxyimino-2-(5-amino-1,2,4-thiadiazol-3-yl)acetamido]-3-(2-thiazolin-2-yl)thiomethyl-3-cephem-4-carboxylic acid (syn isomer). mp 175° to 180° C. (dec.).

I.R. (Nujol): 3350, 3250, 1780, 1680, 1620, 1530 cm$^{-1}$.

N.M.R. (d$_6$-DMSO, δ): 3.43 (2H, m), 3.57 (2H, broad s), 3.93 (3H, s), 4.0–4.5 (4H, m), 5.10 (1H, d, J=4 Hz), 5.80 (1H, dd, J=4 and 8 Hz), 8.10 (2H, s), 9.50 (1H, d, J=8 Hz).

(2) 7-[2-Methoxyimino-2-(5-amino-1,2,4-thiadiazol-3-yl)acetamido]-3-(1-propyl-1H-tetrazol-5-yl)thiomethyl-3-cephem-4-carboxylic acid (syn isomer). mp 155° to 160° C. (dec.)

I.R. (Nujol): 3350, 3250, 1780, 1680, 1630, 1530 cm$^{-1}$.

N.M.R. (d$_6$-DMSO, δ): 0.83 (3H, t, J=7 Hz), 1.80 (2H, sextet, J=7 Hz), 3.67 (2H, broad s), 3.92 (3H, s), 4.23 (2H, t, J=7 Hz), 4.35 (2H, broad s), 5.08 (1H, d, J=4 Hz), 5.78 (1H, dd, J=4 and 8 Hz), 8.08 (2H, s), 9.52 (1H, d, J=8 Hz).

(3) 7-[2-Methoxyimino-2-(5-amino-1,2,4-thiadiazol-3-yl)acetamido]-3-[1-(3-methoxypropyl)-1H-tetrazol-5-yl]thiomethyl-3-cephem-4-carboxylic acid (syn isomer). mp 165° to 167° C. (dec.)

I.R. (Nujol): 3350, 3250, 1780, 1680, 1620, 1530 cm$^{-1}$.

N.M.R. (d$_6$-DMSO, δ): 2.02 (2H, quintet, J=7 Hz), 3.17 (3H, s), 3.30 (2H, t, J=7 Hz), 3.67 (2H, broad s), 3.90 (3H, s), 4.32 (2H, t, J=7 Hz), 4.35 (2H, broad s), 5.10 (1H, d, J=4 Hz), 5.80 (1H, dd, J=4 and 8 Hz), 8.13 (2H, s), 9.57 (1H, d, J=8 Hz).

(4) 7-[2-Methoxyimino-2-(5-amino-1,2,4-thiadiazol-3-yl)acetamido]-3-(3-methyl-1,2,4-thiadiazol-5-yl)thiomethyl-3-cephem-4-carboxylic acid (syn isomer). mp 178° to 182° C. (dec.)

I.R. (Nujol): 3350, 3250, 1780, 1680, 1630, 1530 cm$^{-1}$.

N.M.R. (d$_6$-DMSO, δ): 2.58 (3H, s), 3.60 and 3.77 (2H, ABq, J=17 Hz), 3.97 (3H, s), 4.30 and 4.63 (2H, ABq, J=14 Hz), 5.17 (1H, d, J=4 Hz), 5.85 (1H, dd, J=4 and 8 Hz), 8.13 (2H, s), 9.57 (1H, d, J=8 Hz).

(5) 7-[2-Methoxyimino-2-(5-amino-1,2,4-thiadiazol-3-yl)acetamido]-3-(5-methoxymethyl-1,3,4-thiadiazol-2-yl)thiomethyl-3-cephem-4-carboxylic acid (syn isomer). mp 170° to 174° C. (dec.)

I.R. (Nujol): 3350, 3250, 1780, 1680, 1630, 1530 cm$^{-1}$.

N.M.R. (d$_6$-DMSO, δ): 3.40 (3H, s), 3.70 (2H, broad s), 3.93 (3H, s), 4.27 and 4.70 (2H, ABq, J=13 Hz), 4.83 (2H, s), 5.17 (1H, d, J=4 Hz), 5.83 (1H, dd, J=4 and 8 Hz), 8.12 (2H, s), 9.57 (1H, d, J=8 Hz).

(6) 7-[2-Methoxyimino-2-(5-amino-1,2,4-thiadiazol-3-yl)acetamido]-3-(5-methylthiomethyl-1,3,4-thiadiazol-2-yl)thiomethyl-3-cephem-4-carboxylic acid (syn isomer). mp 173° to 175° C. (dec.)

I.R. (Nujol): 3350, 3250, 1780, 1680, 1630, 1530 cm$^{-1}$.

N.M.R. (d$_6$-DMSO, δ): 2.13 (3H, s), 3.70 (2H, broad s), 3.97 (3H, s), 4.17 (2H, s), 4.27 and 4.57 (2H, ABq, J=14 Hz), 5.17 (1H, d, J=4 Hz), 5.85 (1H, dd, J=4 and 8 Hz), 8.15 (2H, s), 9.58 (1H, d, J=8 Hz).

(7) 7-[2-Methoxyimino-2-(5-amino-1,2,4-thiadiazol-3-yl)acetamido]-3-(4-propyl-4H-1,2,4-triazol-3-yl)thiomethyl-3-cephem-4-carboxylic acid (syn isomer). mp 182° to 184° C. (dec.)

I.R. (Nujol): 3350, 3250, 1780, 1680, 1620, 1530 cm$^{-1}$.

N.M.R. (d$_6$-DMSO, δ): 0.83 (3H, t, J=7 Hz), 1.72 (2H, m), 3.67 (2H, broad s), 3.90 (2H, t, J=7 Hz), 3.93 (3H, s), 4.20 (2H, broad s), 5.10 (1H, d, J=4 Hz), 5.80 (1H, dd, J=4 and 8 Hz), 8.12 (2H, s), 8.63 (1H, s), 9.57 (1H, d, J=8 Hz).

(8) 7-[2-Methoxyimino-2-(5-amino-1,2,4-thiadiazol-3-yl)acetamido]-3-(1-methylthiomethyl-1H-tetrazol-5-yl)thiomethyl-3-cephem-4-carboxylic acid (syn isomer). mp 175° to 178° C. (dec.)

I.R. (Nujol): 3350, 3250, 1780, 1680, 1620, 1530 cm$^{-1}$.

N.M.R. (d$_6$-DMSO, δ): 2.17 (3H, s), 3.72 (2H, broad s), 3.93 (3H, s), 4.30 and 4.50 (2H, ABq, J=13 Hz), 5.13 (1H, d, J=4 Hz), 5.53 (2H, s), 5.83 (1H, dd, J=4 and 8 Hz), 8.12 (2H, s), 9.57 (1H, d, J=8 Hz).

(9) 7-[2-Methoxyimino-2-(5-amino-1,2,4-thiadiazol-3-yl)acetamido]-3-(1-isopropyl-1H-tetrazol-5-yl)thiomethyl-3-cephem-4-carboxylic acid (syn isomer). mp 180° to 182° C. (dec.)

I.R. (Nujol): 3350, 3250, 1780, 1680, 1630, 1530 cm$^{-1}$.

N.M.R. (d$_6$-DMSO, δ): 1.48 (6H, d, J=6 Hz), 3.70 (2H, broad s), 3.93 (3H, s), 4.43 (2H, broad, s), 4.75 (1H, m), 5.13 (1H, d, J=4 Hz), 5.82 (1H, dd, J=4 and 8 Hz), 8.12 (2H, s), 9.57 (1H, d, J=8 Hz).

(10) 7-[2-Methoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer). mp 170° to 175° C. (dec.)

I.R. (Nujol): 3350, 3250, 1780, 1680, 1625, 1530 cm$^{-1}$.

N.M.R. (d$_6$-DMSO, δ): 3.67 (2H, broad s), 3.73 (2H, broad s), 3.90 (3H, s), 4.27 (2H, broad s), 4.33 (2H, broad s), 5.10 (1H, d, J=4 Hz), 5.80 (1H, dd, J=4 and 8 Hz), 8.07 (2H, s), 9.53 (1H, d, J=8 Hz).

(11) 7-[2-Methoxyimino-2-(5-amino-1,2,4-thiadiazol-3-yl)acetamido]-3-[5-(2-hydroxyethyl)-1,3,4-thiadiazol-2-yl]thiomethyl-3-cephem-4-carboxylic acid (syn isomer). mp 175° to 180° C. (dec.)

I.R. (Nujol): 3350, 3250, 1780, 1680, 1630, 1530 cm$^{-1}$.

N.M.R. (d$_6$-DMSO, δ): 3.20 (2H, t, J=5 Hz), 3.67 (2H, broad s), 3.73 (2H, t, J=5 Hz), 3.95 (3H, s), 4.27 and 4.57 (2H, ABq, J=13 Hz), 5.17 (1H, d, J=4 Hz), 5.83 (1H, dd, J=4 and 8 Hz), 8.13 (2H, s), 9.58 (1H, d, J=8 Hz).

(12) 7-[2-Methoxyimino-2-(5-amino-1,2,4-thiadiazol-3-yl)acetamido]-3-(5-propyl-1,3,4-thiadiazol-2-yl)thiomethyl-3-cephem-4-carboxylic acid (syn isomer). mp 177° to 180° C. (dec.)

I.R. (Nujol): 3350, 3250, 1780, 1680, 1630, 1530 cm$^{-1}$.

N.M.R. (d$_6$-DMSO, δ): 0.97 (3H, t, J=7 Hz), 1.73 (2H, m), 3.07 (2H, t, J=7 Hz), 3.70 (2H, broad s), 3.97 (3H, s), 4.37 and 4.57 (2H, ABq, J=13 Hz), 5.17 (1H, d, J=4 Hz), 5.83 (1H, dd, J=4 and 8 Hz), 8.13 (2H, s), 9.57 (1H, d, J=8 Hz).

(13) 7-[2-Methoxyimino-2-(5-amino-1,2,4-thiadiazol-3-yl)acetamido]-3-(5-hydroxymethyl-1,3,4-thiadiazol-2-yl)thiomethyl-3-cephem-4-carboxylic acid (syn isomer). mp 165° to 170° C. (dec.)

I.R. (Nujol): 3350, 3250, 1780, 1680, 1620, 1530 cm$^{-1}$.

N.M.R. (d$_6$-DMSO, δ): 3.67 (2H, broad s), 3.92 (3H, s), 4.27 and 4.57 (2H, ABq, J=13 Hz), 4.82 (2H, s), 5.13 (1H, d, J=4 Hz), 5.83 (1H, dd, J=4 and 8 Hz), 8.17 (2H, s), 9.60 (1H, d, J=8 Hz).

(14) 7-[2-Methoxyimino-2-(5-amino-1,2,4-thiadiazol-3-yl)acetamido]-3-(5-methanesulfonamidomethyl-1,3,4-thiadiazol-2-yl)thiomethyl-3-cephem-4-carboxylic acid (syn isomer). mp 170° to 175° C. (dec.).

I.R. (Nujol): 3350, 3250, 1780, 1680, 1620, 1530 cm$^{-1}$.

N.M.R. (d$_6$-DMSO, δ): 3.00 (3H, s), 3.67 (2H, broad s), 3.93 (3H, s), 4.27 and 4.53 (2H, ABq, J=14 Hz), 4.55 (2H, d, J=6 Hz), 5.13 (1H, d, J=4 Hz), 5.80 (1H, dd, J=4 and 8 Hz), 8.03 (1H, t, J=6 Hz), 8.10 (2H, s), 9.53 (1H, d, J=8 Hz).

(15) 7-[2-Methoxyimino-2-(5-amino-1,2,4-thiadiazol-3-yl)acetamido]-3-(3-allylthio-1,2,4-thiadiazol-5-yl)thiomethyl-3-cephem-4-carboxylic acid (syn isomer). mp 170° to 173° C. (dec.)

I.R. (Nujol): 3350, 3250, 1780, 1680, 1620, 1530 cm$^{-1}$.

N.M.R. (d$_6$-DMSO, δ): 3.58 and 3.74 (2H, ABq, J=17 Hz), 3.90 (2H, d, J=6 Hz), 3.92 (3H, s), 4.32 and 4.54 (2H, ABq, J=14 Hz), 5.15 (1H, d, J=4 Hz), 5.0–5.4 (2H, m), 5.7–6.1 (1H, m), 5.84 (1H, dd, J=4 and 8 Hz), 8.12 (2H, s), 9.58 (1H, d, J=8 Hz).

(16) 7-[2-Methoxyimino-2-(5-amino-1,2,4-thiadiazol-3-yl)acetamido]-3-(5-mesylmethyl-1,3,4-thiadiazol-2-yl)thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

N.M.R. (d$_6$-DMSO, δ): 3.13 (3H, s), 3.70 (2H, broad s), 3.93 (3H, s), 4.15 and 4.63 (2H, ABq, J=13 Hz), 5.17 (2H, s), 5.13 (1H, d, J=4 Hz), 5.83 (1H, dd, J=4 and 8 Hz), 8.08 (2H, s), 9.53 (1H, d, J=8 Hz).

(17) 7-[2-Methoxyimino-2-(5-amino-1,2,4-thiadiazol-3-yl)acetamido]-3-(4-methyl-4H-1,2,4-triazol-3-yl)thiomethyl-3-cephem-4-carboxylic acid (syn isomer). mp 180° to 185° C. (dec.)

I.R. (Nujol): 3350, 3250, 1780, 1680, 1620, 1530 cm$^{-1}$.

N.M.R. (d$_6$-DMSO, δ): 3.53 (3H, s), 3.62 (2H, broad s), 3.87 (3H, s), 4.08 (2H, broad s), 5.07 (1H, d, J=4 Hz), 5.75 (1H, dd, J=4 and 8 Hz), 8.08 (2H, s), 8.52 (1H, s), 9.50 (1H, d, J=8 Hz).

(18) 7-[2-Methoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer). mp 185° to 190° C. (dec.)

I.R. (Nujol): 3350, 3250, 1780, 1680, 1620, 1530 cm$^{-1}$.

N.M.R. (d$_6$-DMSO, δ): 2.47 (6H, s), 3.0–3.3 (2H, m), 3.67 (2H, broad s), 3.90 (3H, s), 4.28 (2H, broad s), 4.4–4.7 (2H, m), 5.08 (1H, d, J=4 Hz), 5.77 (1H, dd, J=4 and 8 Hz), 8.12 (2H, s), 9.55 (1H, d, J=8 Hz).

(19) 7-[2-Methoxyimino-2-(5-amino-1,2,4-thiadiazol-3-yl)acetamido]-3-[4-(3-methoxypropyl)-4H-1,2,4-triazol-3-yl]thiomethyl-3-cephem-4-carboxylic acid (syn isomer). mp 175° to 180° C. (dec.)

I.R. (Nujol): 3350, 3250, 1780, 1680, 1620, 1530 cm$^{-1}$.

N.M.R. (d$_6$-DMSO, δ): 1.97 (2H, m), 3.28 (3H, s), 3.35 (2H, t, J=8 Hz), 3.73 (2H, broad s), 3.97 (3H, s), 4.03 (2H, t, J=8 Hz), 4.23 (2H, broad s), 5.17 (1H, d, J=4 Hz), 5.83 (1H, dd, J=4 and 8 Hz), 8.15 (2H, s), 8.67 (1H, s), 9.57 (1H, d, J=8 Hz).

(20) 7-[2-Methoxyimino-2-(5-amino-1,2,4-thiadiazol-3-yl)acetamido]-3-[5-(2-aminoethyl)-1,3,4-thiadiazol-2-yl]thiomethyl-3-cephem-4-carboxylic acid (syn isomer). mp 205° to 210° C. (dec.)

I.R. (Nujol): 3200, 1770, 1670, 1620, 1530 cm$^{-1}$.

N.M.R. (d$_6$-DMSO, δ): 3.10–3.70 (6H, m), 3.92 (3H, s), 4.50 (2H, broad s), 5.06 (1H, d, J=4 Hz), 5.72 (1H, dd, J=4 and 8 Hz), 8.18 (2H, s), 9.50 (1H, d, J=8 Hz).

(21) 7-[2-Methoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 210° to 215° C. (dec.)

I.R. (Nujol): 3350, 3200, 1770, 1680, 1620 cm$^{-1}$.

(22) 7-[2-Methoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 200° to 205° C. (dec.)

I.R. (Nujol): 3350, 3200, 1775, 1670, 1620, 1530 cm$^{-1}$.

(23) 7-[2-Ethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 150° to 155° C. (dec.)

I.R. (Nujol): 3350, 3230, 1775, 1680, 1620, 1530 cm$^{-1}$.

(24) 7-[2-Isopropoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 145° to 150° C. (dec.)

I.R. (Nujol): 3370, 3230, 1780, 1680, 1625, 1530 cm$^{-1}$.

(25) 7-[2-Propoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 133° C. (dec.)

I.R. (Nujol): 3380, 3230, 1780, 1680, 1625, 1530 cm$^{-1}$.

(26) 7-[2-Methoxyimino-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer). mp 150° to 155° C. (dec.)

I.R. (Nujol): 3350, 3250, 1780, 1670 cm$^{-1}$.

(27) 7-[2-Methoxyimino-2-(5-amino-1,2,4-thiadiazol-3-yl)acetamido]-3-(5-allylthio-1,3,4-thiadiazol-2-yl)thiomethyl-3-cephem-4-carboxylic acid (syn isomer). mp 160° to 165° C. (dec.)

I.R (Nujol): 3350, 3250, 1780, 1680, 1620 cm$^{-1}$.

(28) 7-[2-Methoxyimino-2-(5-amino-1,2,4-thiadiazol-3-yl)acetamido]-3-acetylthiomethyl-3-cephem-4-carboxylic acid (syn isomer). mp. 178° to 182° C. (dec.)

I.R. (Nujol): 3350, 3250, 1780, 1680, 1620 cm$^{-1}$.

(29) 7-[2-Ethoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer). mp 183° to 188° C. (dec.)

I.R. (Nujol): 3370, 3240, 1780, 1690, 1630, 1530, 1380, 1260, 1170, 1040 cm$^{-1}$.

N.M.R. (d$_6$-DMSO, δ): 1.27 (3H, t, J=7 Hz), 1.38 (9H, s), 2.0 (2H, m), 2.98 (2H, m), 3.7 (2H, m), 4.0–4.42 (6H, m), 5.17 (1H, d, J=4.5 Hz), 5.83 (1H, dd, J=4.5 and 8.0 Hz), 6.83 (1H, m), 8.13 (2H, broad s), 9.53 (1H, d, J=8.0 Hz).

(30) 7-[2-Ethoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer).

I.R. (Nujol): 3360, 3240, 1780, 1690, 1630, 1530, 1375, 1250, 1170, 1040 cm$^{-1}$.

N.M.R. (d$_6$-DMSO, δ): 1.27 (3H, t, J=7 Hz), 1.33 (9H, s), 3.17–4.0 (6H, m), 4.01–4.5 (4H, m), 5.17 (1H, d, J=4.5 Hz), 5.87 (1H, dd, J=4.5 and 8.0 Hz), 7.0 (1H, m), 8.16 (2H, broad s), 9.57 (1H, d, J=8.0 Hz).

(31) 7-[2-Ethoxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp. 156° to 159° C. (dec.)

I.R. (Nujol): 3360, 3250, 1780, 1680, 1625, 1380, 1080, 1040 cm$^{-1}$.

N.M.R. (d$_6$-DMSO, δ): 1.27 (3H, t, J=7 Hz), 3.7 (2H, broad s), 3.95 (3H, s), 4.0–4.56 (4H, m), 5.15 (1H, d, J=4.5 Hz), 5.83 (1H, dd, J=4.5 and 8 Hz), 8.12 (2H, broad s), 9.53 (1H, d, J=8.0 Hz).

(32) 7-[2-Ethoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer). mp 177° to 180° C. (dec.)

I.R. (Nujol): 3380, 3250, 1775, 1670, 1620, 1535, 1380, 1040 cm$^{-1}$.

N.M.R. (d$_6$-DMSO, δ): 1.27 (3H, t, J=7 Hz), 2.50 (6H, s), 3.17 (2H, m), 3.67 (2H, m), 4.22 (2H, q, J=7 Hz), 4.0–4.7 (4H, m), 5.13 (1H, d, J=4.5 Hz), 5.83 (1H, dd, J=4.5 and 8.0 Hz), 8.17 (2H, broad s), 9.58 (1H, d, J=8.0 Hz).

(33) 7-[2-Ethoxyimino-2-(5-amino-1,2,4-thiadiazol-3-yl)acetamido]-3-(1-allyl-1H-tetrazol-5-yl)thiomethyl-3-cephem-4-carboxylic acid (syn isomer). mp 160° to 165° C. (dec.)

I.R. (Nujol): 3380, 3250, 1780, 1680, 1630, 1530, 1380, 1040 cm$^{-1}$.

N.M.R. (d$_6$-DMSO, δ): 1.25 (3H, t, J=7 Hz), 3.7 (2H, m), 4.0–6.0 (13H, m), 8.13 (2H, broad s), 9.57 (1H, d, J=8.0 Hz).

(34) 7-[2-Ethoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer). mp 180° to 185° C. (dec.)

I.R. (Nujol): 3350, 3240, 1780, 1680, 1620, 1530, 1380, 1040 cm$^{-1}$.

N.M.R. (d$_6$-DMSO, δ): 1.27 (3H, t, J=7 Hz), 3.77 (2H, m), 4.20 (2H, q, J=7 Hz), 4.20 and 4.67 (2H, ABq, J=12 Hz), 5.20 (1H, d, J=4.5 Hz), 5.83 (1H, dd, J=4.5 and 8 Hz), 7.73 (1H, d, J=9 Hz), 8.12 (2H, broad s), 8.56 (1H, d, J=9 Hz), 9.53 (1H, d, J=8 Hz).

(35) 7-[2-Ethoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 198° to 205° C. (dec.)

I.R. (Nujol): 3350, 3250, 1775, 1680, 1620, 1535, 1380, 1040 cm$^{-1}$.

N.M.R. (d$_6$-DMSO+D$_2$O, δ): 1.27 (3H, t, J=7 Hz), 3.6 (2H, broad s), 4.23 (2H, q, J=7 Hz), 4.0–4.83 (4H, m), 5.13 (1H, d, J=4.5 Hz), 5.80 (1H, d, J=4.5 Hz).

(36) 7-[2-Ethoxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer). mp 170° to 173° C. (dec.)

I.R. (Nujol): 3350, 3240, 1780, 1675, 1625, 1530, 1380, 1040, 720 cm$^{-1}$.

N.M.R. (d$_6$-DMSO, δ): 1.27 (3H, t, J=7 Hz), 3.67–4.4 (10H, m), 5.15 (1H, d, J=4.5 Hz), 5.83 (1H, dd, J=4.5 and 8 Hz), 8.13 (2H, broad s), 9.57 (1H, d, J=8.0 Hz).

(37) 7-[2-Methoxyimino-2-(5-amino-1,2,4-thiadiazol-3-yl)acetamido]-3-(4-allyl-4H-1,2,4-triazol-3-yl)thiomethyl-3cephem-4-carboxylic acid (syn isomer). mp 185° to 190° C. (dec.)

I.R. (Nujol): 3350, 3250, 1780, 1680, 1625, 1530 cm$^{-1}$.

N.M.R. (d$_6$-DMSO, δ): 3.67 (2H, broad s), 3.93 (3H, s), 4.20 (2H, broad s), 4.43–4.66 (2H, m), 4.88–5.40 (3H, m), 5.60–6.06 (2H, m), 8.18 (2H, s), 8.63 (1H, s), 9.57 (1H, d, J=8 Hz).

(38) 7-[2-Methoxyimino-2-(5-amino-1,2,4-thiadiazol-3-yl)acetamido]-3-(3-methoxycarbonyl-1,2,4-thiadiazol-5-yl)thiomethyl-3-cephem-4-carboxylic acid (syn isomer). mp 180° to 185° C. (dec.)

I.R. (Nujol): 3350, 3250, 1780, 1740, 1680, 1620, 1530 cm$^{-1}$.

N.M.R. (d$_6$-DMSO, δ): 3.70 (2H, broad s), 3.93 (6H, s), 4.47 (2H, broad s), 5.17 (1H, d, J=4 Hz), 5.83 (1H, dd, J=4 and 8 Hz), 8.10 (2H, s), 9.57 (1H, d, J=8 Hz).

(39) 7-[2-Methoxyimino-2-(5-amino-1,2,4-thiadiazol-3-yl)acetamido]-3-(3-carboxy-1,2,4-thiadiazol-5-yl)thiomethyl-3-cephem-4-carboxylic acid (syn isomer). mp 175° to 180° C. (dec.)

I.R. (Nujol): 3350, 3250, 1780, 1730, 1680, 1620, 1530 cm$^{-1}$.

N.M.R. (d$_6$-DMSO, δ): 3.73 (2H, broad s), 3.93 (3H, s), 4.47 (2H, broad s), 5.17 (1H, d, J=4 Hz), 5.83 (1H, dd, J=4 and 8 Hz), 8.10 (2H, s), 9.57 (1H, d, J=8 Hz).

(40) 7-[2-Ethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer). mp 182° to 185° C. (dec.)

I.R. (Nujol): 3350, 3200, 1770, 1670, 1620, 1530, 1380, 1040 cm$^{-1}$.

(41) 7-[2-Ethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 195° to 210° C. (dec.)

I.R. (Nujol): 3340, 3210, 1770, 1675, 1620, 1530, 1380, 1040 cm$^{-1}$.

(42) 7-[2-(Isopropoxyimino-2-(5-amino-1,2,4-thiadiazol-3-yl)acetamido]-3-(1-carboxymethyl-1H-tetrazol-5yl)thiomethyl-3-cephem-4-carboxylic acid (syn isomer), mp. 175° to 180° C. (dec.).

I.R. (Nujol): 3300, 3200, 1770, 1720, 1680, 1620, 1520 cm$^{-1}$.

N.M.R. (d$_6$-DMSO, δ): 1.27 (6H, d, J=6 Hz), 3.67 (2H, broad s), 4.23 and 4.47 (2H, ABq, J=14 Hz), 4.20–4.50 (1H, m), 5.10 (1H, d, J=4 Hz), 5.30 (2H, s), 5.80 (1H, dd, J=4 and 8 Hz), 8.10 (2H, s), 9.47 (1H, d, J=8 Hz).

(43) 7-[2-Methoxyimino-2-(5-amino-1,2,4-thiadiazol-3-yl)acetamido]-3-(5-carboxymethylthio-1,3,4-thiadiazol-2-yl)thiomethyl-3-cephem-4-carboxylic acid (syn isomer), mp. 150° to 155° C. (dec.).

I.R. (Nujol): 3350, 3250, 1780, 1720, 1680, 1620, 1530 cm$^{-1}$.

N.M.R. (d$_6$-DMSO, δ): 3.60 and 3.72 (2H, ABq, J=18 Hz), 3.92 (3H, s), 4.14 (2H, s), 4.22 and 4.48 (2H, ABq, J=14 Hz), 5.12 (1H, d, J=4 Hz), 5.80 (1H, dd, J=4 and 8 Hz), 8.50 (2H, s), 9.50 (1H, d, J=8 Hz).

(44) 7-[2-Isopropoxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp. 170° to 175° C. (dec.).

I.R. (Nujol): 3350, 3250, 1780, 1680, 1620, 1530 cm$^{-1}$.

N.M.R. (d$_6$-DMSO, δ): 1.27 (6H, d, J=6 Hz), 3.73 (2H, broad s), 4.00 (3H, s), 4.33 (2H, broad s), 4.27–4.67 (1H, m), 5.17 (1H, d, J=4 Hz), 5.87 (1H, dd, J=4 and 8 Hz), 8.15 (2H, s), 9.53 (1H, d, J=8 Hz).

(45) 7-[2-Isopropoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp. 142° to 147° C. (dec.).

I.R. (Nujol): 3350, 3250, 1780, 1690, 1630, 1530 cm$^{-1}$.

N.M.R. (d$_6$-DMSO, δ): 1.22 (6H, d, J=6 Hz), 1.30 (9H, s), 3.17–3.50 (2H, m), 3.70 (2H, broad s), 4.17–4.57 (5H, m), 5.13 (1H, d, J=4 Hz), 5.83 (1H, dd, J=4 and 8 Hz), 8.17 (2H, s), 9.55 (1H, d, J=8 Hz).

(46) 7-[2-Isopropoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 165° to 170° C. (dec.).

I.R. (Nujol): 3300, 3200, 1775, 1710, 1670, 1625, 1525 cm$^{-1}$.

N.M.R. (d$_6$-DMSO, δ): 1.23 (6H, d, J=6 Hz), 3.73 (2H, broad s), 4.20–4.50 (1H, m), 4.25 and 4.62 (2H, ABq, J=13 Hz), 5.18 (1H, d, J=5 Hz), 5.87 (1H, dd, J=5 and 8 Hz), 7.78 (1H, d, J=10 Hz), 8.18 (2H, broad s), 8.63 (1H, d, J=10 Hz), 9.63 (1H, d, J=8 Hz).

(47) 7-[2-Isopropoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp. 135° to 140° C. (dec.).

I.R. (Nujol): 3350, 3230, 1780, 1680, 1625, 1530 cm$^{-1}$.

N.M.R. (d$_6$-DMSO, δ): 1.27 (6H, d, J=6 Hz), 3.68 (2H, broad s), 4.25 and 4.45 (2H, ABq, J=13 Hz), 4.20–4.50 (1H, m), 4.85–5.08 (2H, m), 5.13 (1H, d, J=5 Hz), 5.18–5.45 (2H, m), 5.82 (1H, dd, J=5 and 8 Hz), 5.60–6.20 (1H, m), 8.12 (2H, broad s), 9.48 (1H, d, J=8 Hz).

(48) 7-[2-Methoxyimino-2-(5-amino-1,2,4-thiadiazol-3-yl)acetamido]-3-(5-trifluoromethyl-1,3,4-thiadiazol-2-yl)thiomethyl-3-cephem-4-carboxylic acid (syn isomer), mp. 150° to 155° C. (dec.).

I.R. (Nujol): 3300, 3200, 1770, 1670, 1620, 1520 cm$^{-1}$.

N.M.R. (d$_6$-DMSO, δ): 3.70 (2H, broad s), 3.93 (3H, s), 4.37 and 4.65 (2H, ABq, J=13 Hz), 5.17 (1H, d, J=5 Hz), 5.85 (1H, dd, J=5 and 8 Hz), 8.17 (2H, broad s), 9.57 (1H, d, J=8 Hz).

(49) 7-[2-Methoxyimino-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp. 205° to 210° C. (dec.).

I.R. (Nujol): 3300, 1765, 1710, 1680, 1620, 1550, 1520 cm$^{-1}$.

N.M.R. (d$_6$-DMSO, δ): 3.67 (2H, broad s), 3.93 (3H, s), 4.27 (2H, broad s), 4.63 (2H, s), 5.10 (1H, d, J=5 Hz), 5.75 (1H, dd, J=5 and 8 Hz), 7.05 (1H, d, J=10 Hz), 7.67 (1H, d, J=10 Hz), 8.13 (2H, broad s), 9.53 (1H, d, J=8 Hz).

(50) 7-[2-Methoxyimino-2-(5-amino-1,2,4-thiadiazol-3-yl)acetamido]-3-(5-methylamino-1,3,4-thiadiazol-2-yl)thiomethyl-3-cephem-4-carboxylic acid (syn isomer), mp. 175° to 180° C. (dec.).

I.R. (Nujol): 3450, 3370, 3250, 1775, 1710, 1680, 1630, 1560 cm$^{-1}$.

N.M.R. (d$_6$-DMSO, δ): 2.90 (3H, s), 3.68 (2H, broad s), 3.95 (3H, s), 4.10 and 4.27 (2H, ABq, J=13 Hz), 5.13 (1H, d, J=5 Hz), 5.83 (1H, dd, J=5 and 8 Hz), 7.83 (1H, broad s), 8.17 (2H, broad s), 9.60 (1H, d, J=8 Hz).

(51) 7-[2-Methoxyimino-2-(5-amino-1,2,4-thiadiazol-3-yl)acetamido]-3-(5-amino-1,3,4-thiadiazol-2-yl)thiomethyl-3-cephem-4-carboxylic acid (syn isomer), mp. 165° to 170° C. (dec.).

I.R. (Nujol): 3350, 3210, 1770, 1670, 1620, 1520 cm$^{-1}$.

N.M.R. (d$_6$-DMSO, δ): 3.67 (2H, broad s), 3.95 (3H, s), 4.08 and 4.25 (2H, ABq, J=13 Hz), 5.12 (1H, d, J=5 Hz), 5.80 (1H, dd, J=5 and 8 Hz), 7.33 (2H, broad s), 8.15 (2H, broad s), 9.57 (2H, d, J=8 Hz).

(52) 7-[2-Methoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp. 175° to 180° C. (dec.).

I.R. (Nujol): 3370, 3250, 1785, 1690, 1630, 1530 cm$^{-1}$.

N.M.R. (d$_6$-DMSO, δ): 1.37 (9H, s), 1.73–2.17 (2H, m), 2.73–3.17 (2H, m), 3.68 (2H, broad s), 3.90 (3H, s), 4.25 (2H, t, J=7 Hz), 4.27 (2H, broad s), 5.12 (1H, d, J=5 Hz), 5.80 (1H, dd, J=5 and 8 Hz), 6.70–7.02 (1H, m), 8.13 (2H, broad s), 9.55 (1H, d, J=8 Hz).

(53) 7-[2-Methoxyimino-2-(5-amino-1,2,4-thiadiazol-3-yl)acetamido]-3-[1-{3-(acetamido)propyl}-1H-tetrazol-5-yl]thiomethyl-3-cephem-4-carboxylic acid (syn isomer), mp. 150° to 155° C. (dec.).

I.R. (Nujol): 3350, 3230, 1780, 1660, 1620, 1530 cm$^{-1}$.

N.M.R. (d₆-DMSO, δ): 1.80 (3H, s), 1.87-2.17 (2H, m), 2.90-3.30 (2H, m), 3.70 (2H, broad s), 3.93 (3H, s), 4.28 (2H, t, J=7 Hz), 4.30 (2H, broad s), 5.13 (1H, d, J=5 Hz), 5.82 (1H, dd, J=5 and 8 Hz), 7.77-8.03 (1H, m), 8.10 (2H, broad s), 9.57 (1H, d, J=8 Hz).

(54) 7-[2-Methoxyimino-2-(5-amino-1,2,4-thiadiazol-3-yl)acetamido]-3-[1-{1-(acetamidomethyl)ethyl}-1H-tetrazol-5-yl]thiomethyl-3-cephem-4-carboxylic acid (syn isomer), mp. 160° to 165° C. (dec.).

I.R. (Nujol): 3350, 3250, 1780, 1660, 1620, 1530 cm⁻¹.

N.M.R. (d₆-DMSO, δ): 1.52 (3H, d, J=6 Hz), 1.75 (3H, s), 3.13-3.80 (2H, m), 3.72 (2H, broad s), 3.93 (3H, s), 4.33 (2H, broad s), 4.50-4.83 (1H, m), 5.12 (1H, d, J=5 Hz), 5.80 (1H, dd, J=5 and 8 Hz), 8.00 (1H, t, J=6 Hz), 8.10 (2H, broad s), 9.53 (1H, d, J=8 Hz).

(55) 7-[2-Methoxyimino-2-(5-amino-1,2,4-thiadiazol-3-yl)acetamido]-3-[1-{1-(N-t-butoxycarbonylaminomethyl)ethyl}-1H-tetrazol-5-yl]thiomethyl-3-cephem-4carboxylic acid (syn isomer), mp. 180° to 185° C. (dec.).

I.R. (Nujol): 3370, 3230, 1780, 1690, 1630, 1530 cm⁻¹.

N.M.R. (d₆-DMSO, δ): 1.33 (9H, s), 1.50 (3H, d, J=6 Hz), 3.17-3.60 (2H, m), 3.73 (2H, broad s), 3.93 (3H, s), 4.35 (2H, broad s), 4.33-4.83 (1H, m), 5.17 (1H, d, J−5 Hz), 5.87 (1H, dd, J=5 and 8 Hz), 6.93-7.23 (1H, m), 8.20 (2H, broad s), 9.72 (1H, d, J=8 Hz).

(56) 7-[2-Methoxyimino-2-(5-amino-1,2,4-thiadiazol-3-yl)acetamido]-3-[1-{3-(N,N-dimethylamino)propyl}-1H-tetrazol-5-yl]thiomethyl-3-cephem-4-carboxylic acid (syn isomer), mp. 165° to 170° C. (dec.).

I.R. (Nujol): 3350, 3200, 1770, 1670, 1610, 1530 cm⁻¹.

N.M.R. (d₆-DMSO, δ): 2.03-2.57 (2H, m), 2.67 (6H, s), 2.73-3.27 (2H, m), 3.67 (2H, broad s), 3.93 (3H, s), 4.33 (2H, broad s), 4.10-4.77 (2H, m), 5.05 (1H, d, J=5 Hz), 5.70 (1H, dd, J=5 and 8 Hz), 7.93-8.43 (3H, m), 9.53 (1H, d, J=8 Hz).

(57) 7-[2-Isopropoxyimino-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp. 140° to 145° C. (dec.).

I.R. (Nujol): 3300, 1780, 1670, 1620, 1530 cm⁻¹.

(58) 7-[2-Methoxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp. 150° to 155° C. (dec.).

I.R. (Nujol): 3300, 3150, 1770, 1720, 1670, 1620, 1520 cm⁻¹.

(59) 7-[2-Methoxyimino-2-(5-phosphonoamino-1,2,4-thiadiazol-3-yl)acetamido-3-(1,3,4-thiadiazol-2-yl)thiomethyl-3-cephem-4-carboxylic acid (syn isomer), mp. 140° to 145° C. (dec.).

I.R. (Nujol): 3180, 1765, 1670, 1515 cm⁻¹.

(60) 7-[2-Methoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp. 185° to 190° C. (dec.).

I.R. (Nujol): 3300, 3200, 1770, 1670, 1610, 1530 cm⁻¹.

(61) 7-[2-Isopropoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp. 210° to 215° C. (dec.).

I.R. (Nujol): 3350, 3200, 1750, 1670, 1620, 1530 cm⁻¹.

(62) 7-[2-Isopropoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp. 195° to 200° C. (dec.).

I.R. (Nujol): 3350, 3250, 1775, 1680, 1620, 1530 cm⁻¹.

(63) 7-[2-Methoxyimino-2-(5-amino-1,2,4-thiadiazol-3-yl)acetamido]-3-[1-{1-(aminomethyl)ethyl}-1H-tetrazol-5-yl]thiomethyl-3-cephem-4-carboxylic acid (syn isomer), mp. 190° to 195° C. (dec.).

I.R. (Nujol): 3350, 3230, 1770, 1670, 1620, 1530 cm⁻¹.

(64) 7-[2-Methoxyimino-2-(5-formamido-1,2,4-thiadiazol-3yl)acetamido]-3-(1-methyl-1H-tetrazol-5-ylthiomethyl)-3-cephem-4-carboxylic acid (syn isomer), mp. 170° to 175° C. (dec.).

I.R. (Nujol): 3300, 1780, 1680 cm⁻¹.

(65) 7-[2-Methoxyimino-2-(5-amino-1,2,4-thiadiazol-3-yl)acetamido]-3-(1-methyl-1H-tetrazol-5-ylthiomethyl)-3-cephem-4-carboxylic acid (syn isomer), mp. 170° to 175° C. (dec.).

I.R. (Nujol): 3300, 1770, 1660, 1610, 1520 cm⁻¹.

(66) 7-[2-Methoxyimino-2-(5-amino-1,2,4-thiadiazol-3-yl)acetamido]-3-(5-methyl-1,3,4-thiadiazol-2-ylthiomethyl)-3-cephem-4-carboxylic acid (syn isomer), mp. 175° to 180° C. (dec.).

I.R. (Nujol): 3350, 1780, 1680, 1625, 1530 cm⁻¹.

(67) 7-[2-Methoxyimino-2-(5-amino-1,2,4-thiadiazol-3-yl)acetamido]-3-(1,3,4-thiadiazol-2-ylthiomethyl)-3-cephem-4-carboxylic acid (syn isomer), mp. 172° to 177° C. (dec.).

I.R. (Nujol): 3350, 1775, 1680, 1626, 1630 cm⁻¹.

(68) 7-[2-Methoxyimino-2-(5-amino-1,2,4-thiadiazol-3-yl)acetamido]-3-(1-allyl-1H-tetrazol-5-ylthiomethyl)-3-cephem-4-carboxylic acid (syn isomer), mp. 170° to 172° C. (dec.).

I.R. (Nujol): 3350, 1780, 1680, 1625, 1530 cm⁻¹.

EXAMPLE 22

A solution of 7-[2-methoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer) (2.0 g) in 99% formic acid (20 ml) was stirred for 2.5 hours at ambient temperatures. The mixture was evaporated to dryness and the residue was dissolved in an aqueous solution of sodium bicarbonate and adjusted to pH 3 with 10% hydrochloric acid. A resulting precipitate was filtered off and the filtrate was subjected to column chromatography on non ion adsorption resin (Dianion HP 20) (Trademark: prepared by Mitsubishi Chemical Industries). The column was washed with water and eluted wth 50% aqueous methanol. The eluate was evaporated to remove methanol and then lyophilized to give 7-[2-methoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer) (250 mg). mp 200° to 205° C. (dec.)

I.R. (Nujol): 3350, 3200, 1775, 1670, 1620, 1530 cm⁻¹.

N.M.R. (d₆-DMSO, δ): 3.47 (2H, broad s), 3.60 (2H, broad s), 3.93 (3H, s), 4.2 (2H, broad s), 4.37 (2H, broad s), 4.78 (2H, broad s), 5.03 (1H, d, J=4 Hz), 5.70 (1H, dd, J=4 and 8 Hz), 8.10 (2H, s) 9.50 (1H, d, J=8 Hz).

EXAMPLE 23

A solution of 7-[2-methoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer) (2.22 g) in formic acid (22 ml) was stirred for 2.5 hours at ambient temperature. The reaction mixture was post-treated in a conventional manner to give 7-[2-methoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer) (0.875 g), mp. 185° to 190° C. (dec.).

I.R. (Nujol): 3300, 3200, 1770, 1670, 1610, 1530 cm$^{-1}$.

N.M.R. (d$_6$-DMSO+D$_2$O, δ): 2.0–2.33 (2H, m), 2.67–3.0 (2H, m), 3.40–3.70 (2H, m), 3.93 (3H, s), 4.10–4.67 (4H, m), 5.03 (1H, d, J=5 Hz), 5.75 (1H, d, J=5 Hz).

EXAMPLE 24

The following compounds were obtained according to similar manners to those of Examples 22 and 23.

(1) 7-[2-Methoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 210°–215° C. (dec.)

I.R. (Nujol): 3350, 3200, 1770, 1680, 1620 cm$^{-1}$.

N.M.R. (d$_6$-DMSO, δ): 3.60 (2H, broad s), 3.93 (3H, s), 4.33 and 4.57 (2H, ABq, J=13 Hz), 4.43 (2H, s), 5.10 (1H, d, J=4 Hz), 5.77 (1H, dd, J=4 and 8 Hz), 8.17 (2H, s), 9.50 (1H, d, J=8 Hz).

(2) 7-[2-Methoxyimino-2-(5-amino-1,2,4-thiadiazol-3-yl)acetamido]-3-[5-(2-aminoethyl)1,3,4-thiadiazol-2-yl]thiomethyl-3-cephem-4-carboxylic acid (syn isomer). mp 205° to 210° C. (dec.)

I.R. (Nujol): 3200, 1770, 1670, 1620, 1530 cm$^{-1}$.

(3) 7-[2-Ethoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 198° to 205° C. (dec.)

I.R. (Nujol): 3350, 3250, 1775, 1680, 1620, 1535, 1380, 1040 cm$^{-1}$.

(4) 7-[2-Ethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer). mp 182° to 185° C. (dec.)

I.R. (Nujol): 3350, 3200, 1770, 1670, 1620, 1530, 1380, 1040 cm$^{-1}$.

N.M.R. (d$_6$-DMSO, δ): 1.27 (3H, t, J=7 Hz), 2.17 (2H, m), 2.83 (2H, m), 4.17 (2H, q, J=7 Hz), 3.7–4.7 (6H, m), 5.00 (1H, d, J=4.5 Hz), 5.70 (1H, dd, J=4.5 and 8.0 Hz), 8.17 (2H, broad s), 9.33 (1H, d, J=8.0 Hz).

(5) 7-[2-Ethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 195° to 210° C. (dec.)

I.R. (Nujol): 3340, 3210, 1770, 1675, 1620, 1530, 1380, 1040 cm$^{-1}$.

N.M.R. (d$_6$-DMSO+D$_2$O, δ): 1.26 (3H, t, J=7 Hz), 3.0–3.7 (4H, m), 4.0–4.5 (4H, m), 4.66 (2H, m), 5.03 (1H, d, J=4.5 Hz), 5.70 (1H, d, J=4.5 Hz).

(6) 7-[2-Isopropoxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp. 210° to 215° C. (dec.).

I.R. (Nujol): 3350, 3200, 1750, 1670, 1620, 1530 cm$^{-1}$.

N.M.R. (d$_6$-DMSO, δ): 1.30 (6H, d, J=6 Hz), 3.67 (2H, broad s), 4.20–4.83 (5H, m), 5.13 (1H, d, J=4 Hz), 5.80 (1H, dd, J=4 and 8 Hz), 8.13 (2H, s), 9.43 (1H, d, J=8 Hz).

(7) 7-[2-Isopropoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp. 195° to 200° C. (dec.).

I.R. (Nujol): 3350, 3250, 1775, 1680, 1620, 1530 cm$^{-1}$.

N.M.R. (d$_6$-DMSO, δ): 1.27 (6H, d, J=6 Hz), 3.47 (2H, broad s), 3.67 (2H, broad s), 4.27 (2H, broad s), 4.33–4.57 (1H, m), 4.67 (2H, broad s), 5.10 (1H, d, J=4 Hz), 5.83 (1H, dd, J=4 and 8 Hz), 8.17 (2H, s), 9.47 (1H, d, J=8 Hz).

(8) 7-[2-Methoxyimino-2-(5-amino-1,2,4-thiadiazol-3-yl)acetamido]-3-[1-{1-(aminomethyl)ethyl}-1H-tetrazol-5-yl]thiomethyl-3-cephem-4-carboxylic acid (syn isomer), mp. 190° to 195° C. (dec.).

I.R. (Nujol): 3350, 3230, 1770, 1670, 1620, 1530 cm$^{-1}$.

N.M.R. (d$_6$-DMSO+D$_2$O, δ): 1.23–1.70 (3H, m), 3.10–3.80 (4H, m), 3.92 (3H, s), 4.0–4.5 (3H, m), 5.05 (1H, d, J=5 Hz), 5.73 (1H, d, J=5 Hz).

(9) 7-[2-Methoxyimino-2-(5-amino-1,2,4-thiadiazol-3-yl)acetamido]-3-(5-amino-1,3,4-thiadiazol-2-yl)thiomethyl-3-cephem-4-carboxylic acid (syn isomer), mp. 165° to 170° C. (dec.).

I.R. (Nujol): 3350, 3210, 1770, 1670, 1620, 1520 cm$^{-1}$.

What we claim is:

1. A compound of the formula $$R^1 \underset{S}{\overset{N}{\diagup}} \underset{N}{\overset{}{\diagdown}} C\text{-COOH} \atop \underset{OR^2}{\overset{\parallel}{N}}$$

wherein
R$^1$ is amino or a protected amino and
R$^2$ is lower alkyl,
and its reactive derivative at the carboxy group selected from the group consisting of acid halide, acid anhydride, acid azide, amide and ester, and salt thereof.

2. Syn isomer of a compound of claim 1, wherein the reactive derivative at the carboxy group is acid halide.

3. A compound of claim 2, wherein R$^1$ is amino.

4. A compound of claim 2, wherein R$^1$ is lower alkanoylamino.

5. A compound of claim 3, wherein R$^2$ is methyl, ethyl, propyl or isopropyl.

6. A compound of claim 5, which is 2-methoxyimino-2-(5-amino-1,2,4-thiadiazol-3-yl)acetic acid (syn isomer).

7. A compound of claim 5, which is 2-ethoxyimino-2-(5-amino-1,2,4-thiadiazol-3-yl)acetic acid (syn isomer).

8. A compound of claim 5, which is 2-propoxyimino-2-(5-amino-1,2,4-thiadiazol-3-yl)acetic acid (syn isomer).

9. A compound of claim 5, which is 2-isopropoxyimino-2-(5-amino-1,2,4-thiadiazol-3-yl)acetic acid (syn isomer).

* * * * *